US008302603B1

(12) United States Patent
Weber

(10) Patent No.: US 8,302,603 B1
(45) Date of Patent: Nov. 6, 2012

(54) AIRCREW REBREATHER SYSTEM

(76) Inventor: David W. Weber, South Lyon, MI (US)

( * ) Notice: Subject to any disclaimer, the term of this patent is extended or adjusted under 35 U.S.C. 154(b) by 1265 days.

(21) Appl. No.: 12/077,755

(22) Filed: Mar. 21, 2008

Related U.S. Application Data

(60) Provisional application No. 60/919,451, filed on Mar. 22, 2007.

(51) Int. Cl.
*A61M 16/00* (2006.01)

(52) U.S. Cl. ......... 128/205.17; 128/205.12; 128/204.18; 128/204.28; 128/204.29; 128/205.13; 128/205.27; 128/205.28

(58) Field of Classification Search ............. 128/205.12, 128/200.24, 201.27, 201.28, 202.11, 202.22, 128/204.148, 204.21, 204.22, 204.28, 204.29, 128/205.13–205.17, 205.22, 205.27–205.29, 128/200.22, 203.28; 604/97.01–97.03, 98.01–98.02, 604/99.01, 185, 403, 408; 138/30
See application file for complete search history.

(56) References Cited

U.S. PATENT DOCUMENTS

| | | | | | |
|---|---|---|---|---|---|
| 4,407,153 | A | * | 10/1983 | Furlong et al. | 73/31.04 |
| 4,440,166 | A | * | 4/1984 | Winkler et al. | 128/204.22 |
| 4,821,712 | A | * | 4/1989 | Gossett | 128/205.15 |
| 4,879,996 | A | * | 11/1989 | Harwood et al. | 128/202.26 |
| 5,195,516 | A | * | 3/1993 | Grimsey | 128/204.26 |
| 5,485,834 | A | * | 1/1996 | Joye et al. | 128/205.13 |
| 5,577,498 | A | * | 11/1996 | Yoshida et al. | 128/205.28 |
| 5,924,418 | A | | 7/1999 | Lewis | |
| 5,964,221 | A | | 10/1999 | McKenna | |
| 6,003,513 | A | | 12/1999 | Readey et al. | |
| 6,302,106 | B1 | | 10/2001 | Lewis | |
| 6,341,604 | B1 | * | 1/2002 | Kellon | 128/201.27 |
| 6,408,847 | B1 | | 6/2002 | Nuckols et al. | |
| 6,523,538 | B1 | * | 2/2003 | Wikefeldt | 128/204.18 |
| 2002/0073999 | A1 | * | 6/2002 | Kellon | 128/204.28 |
| 2003/0188744 | A1 | | 10/2003 | Deas et al. | |
| 2004/0200478 | A1 | | 10/2004 | Gordon | |

* cited by examiner

*Primary Examiner* — Justine Yu
*Assistant Examiner* — Colin W Stuart
(74) *Attorney, Agent, or Firm* — MacMillan, Sobanski & Todd, LLC

(57) ABSTRACT

A rebreather system for aircrew that includes a double counter lung having a void between inner and outer bladders that allows selective pressurization of the inner bladder.

7 Claims, 23 Drawing Sheets

FIG. 4A
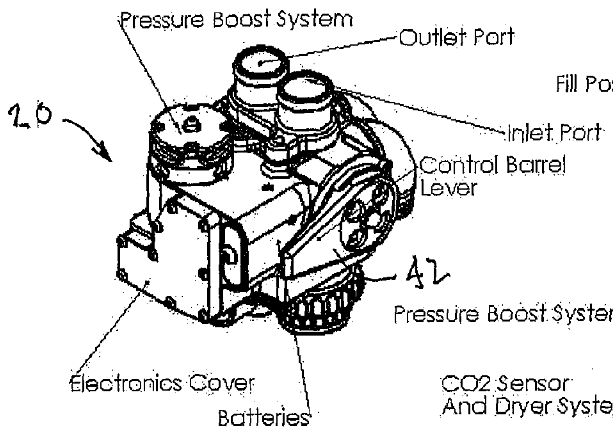
FIG. 4B
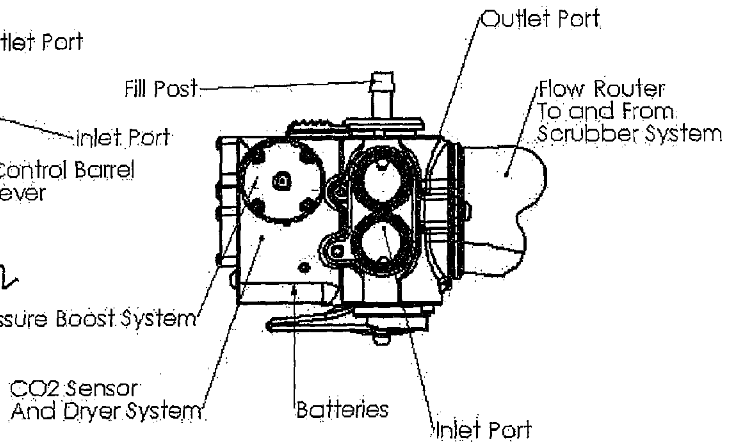
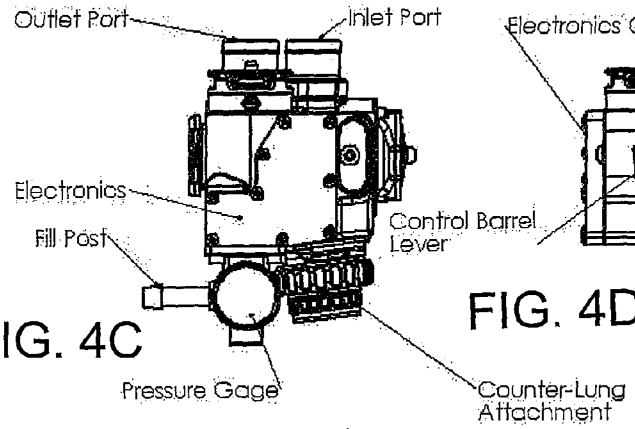
FIG. 4C
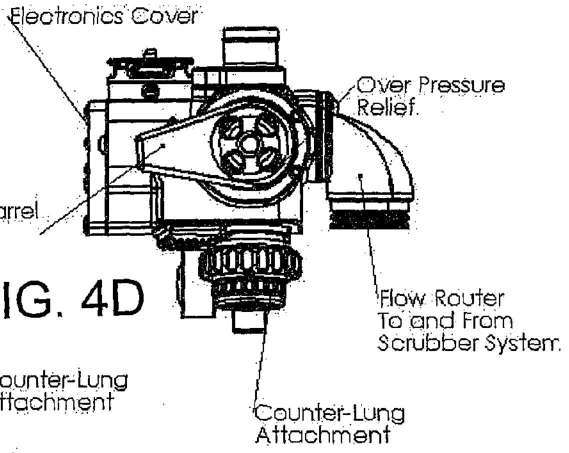
FIG. 4D
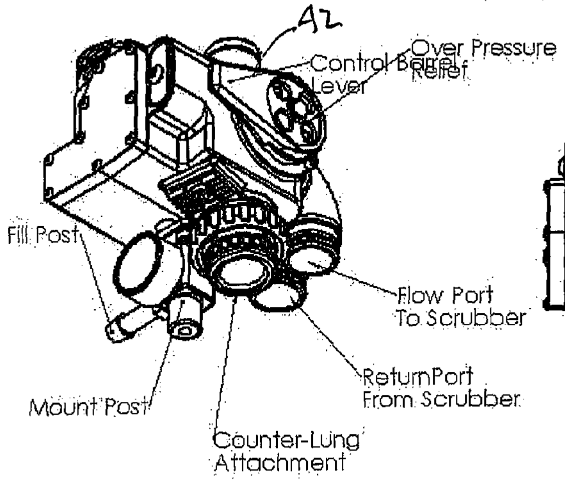
FIG. 4E
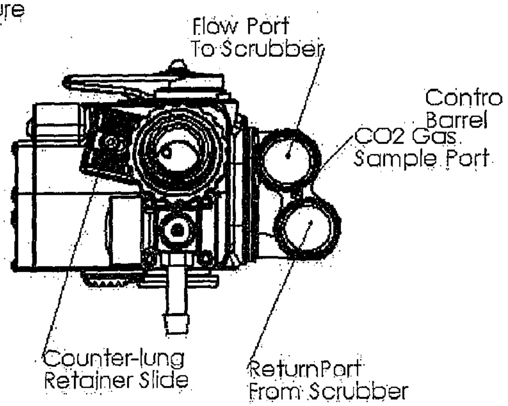
FIG. 4F Inlet
Outlet Outlet Inlet
Outlet
A
A
B
B Inlet
Outlet Outlet
SECTION B-B

SECTION A-A

Inlet
Retainer Lip
Pump Outlet
Retainer Lip
Pump Inlet

SECTION A-A
SCALE 1 : 1

SECTION B-B
SCALE 1 : 1

Oxygen-On

SECTION A-A
SCALE 1 : 1

SECTION B-B
SCALE 1 : 1

Oxygen-On

SECTION A-A
SCALE 1 : 1

SECTION B-B
SCALE 1 : 1

AIRCREW REBREATHER SYSTEM

CROSS-REFERENCE TO RELATED APPLICATIONS

This application claims the benefit of U.S. Provisional Application No. 60/919,451, filed Mar. 22, 2007, the disclosure of which is incorporated herein by reference.

BACKGROUND OF THE INVENTION

The present invention relates generally to self-contained breathing systems and more particularly to closed circuit rebreathers having an oxygen source and a gas scrubbing system.

Traditionally, self-contained breathing apparatuses can be viewed as falling into two general categories; open circuit and closed or semi-closed circuit. Open circuit systems are typically recognized by the common term SCUBA and represent one of the most commonly used forms of breathing apparatus. Developed and popularized by Jacques Cousteau for underwater use, open circuit scuba apparatus generally comprises a high pressure tank filled with compressed air, the tank coupled to a demand regulator which supplies the breathing gas to for example, a diver, at the diver's ambient pressure, thereby allowing the user to breathe the gas with relative ease. Similar systems, such as the Scott Air Pack are utilized by rescue crews for entering buildings that are filled with smoke or other hazardous gases. Likewise, other similar systems are used by aircrew to perform duties in the cabin or cargo area of aircraft when the aircraft is at altitudes that require a supplemental oxygen supply.

Conventional open circuit self contained breathing systems are very well understood in the art and have been developed over the past several years into a wide variety of gas delivery systems, configured for an equally wide variety of applications. For example, compressed air is used as a breathing gas in typical sport diving applications, while one or more artificial mixtures of gasses might comprise the breathing mixture for diving operations at depths greater than approximately 50 meters (150 feet).

While open circuit scuba apparatus is relatively simple, at least in its compressed air form, the equipment required is bulky, heavy and the design itself is inherently inefficient in its use of the breathing gas. Each exhaled breath is expelled to the surrounding environment, thus wasting all the oxygen which was not absorbed by the user during the breath. This inefficiency in breathing gas utilization normally requires a diver to carry a large volume of breathing gas, in order to obtain a reasonable dive time. For example, conventional open circuit scuba gear typically includes compressed air tanks having gas volumes of about 80 cubic feet, and which weigh over 40 lbs. For aircrews, the open circuit functioning of the apparatus means that any inhaled oxygen is exhaled into the surrounding atmosphere. Because of this, it has been estimated that more than 90 percent of the oxygen carried in the apparatus is wasted. Accordingly, flight crews may not have enough useable oxygen to perform needed tasks while the aircraft is at higher altitudes, which may create personnel and flight safety risks.

The most common type of open circuit breathing apparatus is depicted in FIG. 1A and is of the open circuit demand-type which utilizes compressed air tanks in combination with demand regulator valves which provide air from the tanks on demand from a user 118 by the inhalation of air. A compressed air supply tank 110 is coupled to a first stage (high pressure) regulator 112 which conventionally includes an on-off valve 111 which reduces the pressure of the air within the tank to a generally uniform low-pressure value suitable for use by the rest of the system. Low pressure air (approximately 150 psi) is delivered to a second stage IO regulator 114 through a demand valve 116 in conventional fashion. Compressed air, at the cylinder pressure, is reduced to the user's ambient pressure in two stages, with the first stage reducing the pressure below the tank pressure, but above the ambient water pressure, and the second stage reducing the gas pressure to the surrounding ambient or water pressure. The demand valve is typically a diaphragm actuated, lever operated spring-loaded poppet which functions as a one-way valve, opening in the direction of air flow, upon movement of the diaphragm by a diver's inhalation of a breath.

The second form of self contained breathing apparatus is the closed circuit or semi-closed circuit breathing apparatus, commonly termed rebreathers. As the name implies, a rebreather allows a user to "rebreathe" exhaled gas to thus make nearly total use of the oxygen content in its most efficient form. Since only a small portion of the oxygen a person inhales on each breath is actually used by the body, most of this oxygen is exhaled, along with virtually all of the inert gas content such as nitrogen and a small amount of carbon dioxide which is generated by the diver. Rebreather systems make nearly total use of the oxygen content of the supply gas by removing the generated carbon dioxide and by replenishing the oxygen content of the system to make up for that amount consumed by a user.

Both types of rebreather systems mentioned above, comprise a certain few essential components; namely, a flow loop with valves to control the flow direction, a counterlung or breathing bag, a scrubber to absorb or remove exhaled $CO_2$, and some means to add gas to the counterlung as the ambient pressure increases. Valves maintain gas flow within the flow loop in a constant direction and a diver's lungs provides the motive power.

A typical semi-closed circuit rebreather system is illustrated in FIG. 1B and commonly comprises a compressed gas cylinder 120 conventionally including an on-off valve 111 and first stage, high-pressure regulator 112, containing a specific gas mix having a predetermined fraction of oxygen. The gas is provided to a flow loop 122, generally implemented by flexible, gas impermeable hoses, which are coupled between the cylinder 120 and a flexible breathing bag 124, sometimes termed a counterlung. A pair of one-way check valves, 126 and 128, are disposed in the flow loop such that the gas flow within the loop is maintained in a single direction, which is clockwise in the illustration of FIG. 1B. An exhaled breath would thus enter the counterlung, increasing the pressure therein, and pass through one-way check valve 126 and move through some device means to remove excess carbon dioxide from the breathing gas, such as a CO, canister 130, and thereby return to the counterlung through one-way check valve 128. The check valves thus maintain the gas flow in a constant direction, while the user's lungs move the gas through the $CO_2$ canister in the system. The gas mix is introduced into the flow loop at a flow rate calculated to maintain the oxygen needs of a particular user during the operation of the system. Gas is introduced to the flow loop at a constant fixed flow rate through a valve 132 coupled between the flow loop and the first stage regulator 112 of the gas cylinder 120. As the breathing gas mix is recirculated, some of the oxygen is necessarily consumed and CO, is absorbed, thus perturbing both the total volume and the mix of the gas. A portion of the oxygen is consumed during recirculation, so the user necessarily breathes a mixture with a lower oxygen concentration than that of the gas mix. Since the amount of oxygen supplied to the system depends on a user's activity level (oxygen consumption rate), care must be taken to take activity into account as well as selecting the gas mixture composition for a particular diving depth or altitude.

A more efficient type of rebreather system is the closed circuit rebreather, illustrated in simplified form in FIG. 1C. Closed circuit rebreathers are generally more sophisticated and effective in their maintenance of oxygen levels in the flow loop. Nonetheless, they share common components with semi-closed circuit rebreather systems such as that depicted in FIG. 1B. The main contrast between fully closed and semi-closed circuit rebreather systems is that the closed circuit rebreather, as configured, provides a source of pure oxygen to the flow loop and introduces oxygen to the recirculating gas in an amount ideally equal only to that consumed by a user such that system mass is conserved. The oxygen level (more correctly the oxygen partial pressure) is monitored electronically by an oxygen sensor 134 whose output is evaluated by a processing circuit 136 which, in turn, controls an electrically operated solenoid valve so as to add oxygen to the system when the oxygen sensor indicates it is being depleted. It should be noted, that closed circuit rebreathers only introduce gas to the system when the oxygen sensor 134 indicates the need for additional oxygen or as ambient pressure increases during descent and the addition of diluent is required to prevent the collapse of the counterlung. Oxygen is added in "pulses" in contrast to the steady-state flow of the semi-closed circuit system and is required to be constantly monitored. Diluent from an optional diluent gas source (indicated in phantom in FIG. 1C is added by a demand valve in the counterlung that is activated as the counterlung collapses because of increasing ambient pressure. It should likewise be noted that once a particular oxygen partial pressure has been established in a closed circuit rebreather system, this partial pressure of oxygen is maintained by operation of the oxygen sensor 134 and processing circuit 36, regardless of a user's external environment, and any changes thereto.

Partial Pressure of Oxygen (PPO2) in a particular breathing gas mixture may be understood as the pressure that oxygen alone would have if the other gasses (such as nitrogen) were absent from the gas. The physiological effects of oxygen depend upon this partial pressure in the mix and serious consequences result from oxygen partial pressures that are too high; e.g., oxygen becomes increasingly toxic as the partial pressure increases significantly above the oxygen partial pressure found in air at sea level (0.21 atmospheres), as well as too low. When the oxygen partial pressure is too low, a user would not necessarily experience any discomfort or shortness of breath, and in many cases may not even be aware of the shortness of oxygen until unconsciousness is imminent. In a relatively short period of time, depending in turn on the volume of a counterlung, the user would become unconscious and eventually die from hypoxia. The diver would experience very little discomfort, and in fact may feel rather euphoric. This euphoria is a typical and characteristically dangerous aspect of hypoxia.

On the other hand, serious physiological effects may result from too much oxygen leading to various forms of what might be termed oxygen poisoning. There are several major forms of oxygen poisoning but two in particular have a bearing on the operational configuration of various rebreather systems; central nervous system toxicity (CNS) and pulmonary or whole-body oxygen poisoning. Almost any rebreather system that includes an oxygen supply component is capable of delivering excess oxygen to a user. Excess oxygen is defined in this case as oxygen partial pressure greater than specific tolerable limits; the most important limit being that of CNS oxygen toxicity. CNS limits, which define the oxygen partial pressure levels that can be tolerated for various durations depending on the degree of oxygen excess, are defined in the 1991 National Oceanographic and Atmospheric Administration (NOAA) diving manual and are well understood by those skilled in the art. CNS poisoning becomes a significant consideration as the partial pressure of oxygen exceeds a generally accepted limit of 1.6 atmospheres. CNS toxicity gives rise to various symptoms, the most serious of which are convulsive seizures, similar to those experienced during an epileptic fit. These seizures generally last for about 2 minutes and are followed by a period of unconsciousness.

If a pressure level of 1.6 atmospheres is not exceeded, then the concern becomes one of pulmonary or whole body toxicity rather than CNS. Pulmonary oxygen toxicity results from prolonged exposure to oxygen partial pressures above approximately 0.5 atmospheres and the consequences of excessive exposure include lung irritation, which may be reversible, and some lung damage which is not.

Thus, there is no one specific partial pressure of oxygen in a breathing gas that is optimal for all conditions at all depths or altitudes. One set of factors would tend to indicate that a relatively higher partial pressure of oxygen is preferred, while another set of factors would tend to indicate that this is not always the case.

Regarding aircrew usage of portable breathing systems, as described above, current low pressure oxygen bottles do not provide enough emergency oxygen for aircrews to perform their duties. Simply making the oxygen tank larger is not a practical solution since, as the tank size increases, so does the hindrance to the aircrew. Additionally, the weight and size of the supplemental breathing apparatus needs to be kept to a minimum. A standard oxygen tank filled to 450 psi holds approximately 145 liters of oxygen and is only useful for about 25 minutes when operated in a demand mode. Therefore, it would be desirable to provide an improved rebreather system for aircrews.

SUMMARY OF THE INVENTION

This invention relates to enhanced closed circuit rebreathers having an oxygen source and a gas scrubbing system for use by aircrews.

The present invention contemplates a rebreather system having a control unit connected to a couterlung with the control unit having a hose connector mounted thereupon. The system also includes a supply of oxygen gas connected to the counterlung and a scrubber canister connected to both the control unit and the counterlung. A breathing hose connector is mounted upon said control unit and control valves are disposed within said control unit that are operative to selectively add oxygen gas to the conterlung. A control device is disposed within the control unit and connected to the control valves and is operative to selectively actuate the valves to maintain the oxygen level within the system as function of the surrounding environment.

The present invention also contemplates that the couterlung a double counterlung that includes an inner air bladder disposed within an outer air bladder with a void defined between said inner and outer bladders. Furthermore, the void between the inner and outer bladders is selectively pressurized by the control unit to provide a pressure boost to the inner counterlung bladder.

Various objects and advantages of this invention will become apparent to those skilled in the art from the following detailed description of the preferred embodiment, when read in light of the accompanying drawings.

BRIEF DESCRIPTION OF THE DRAWINGS

FIG. 4A shows a perspective view from above of the head assembly shown in FIG. 3.

FIG. 4B shows a top view of the head assembly shown in FIG. 3.

FIG. 4C shows a rear view of the head assembly shown in FIG. 3.

FIG. 4D shows a side view of the head assembly shown in FIG. 3.

FIG. 4E shows a perspective view from below of the head assembly shown in FIG. 3.

FIG. 4F shows a bottom view of the head assembly shown in FIG. 3.

DETAILED DESCRIPTION OF THE PREFERRED EMBODIMENT

Figure 2A:
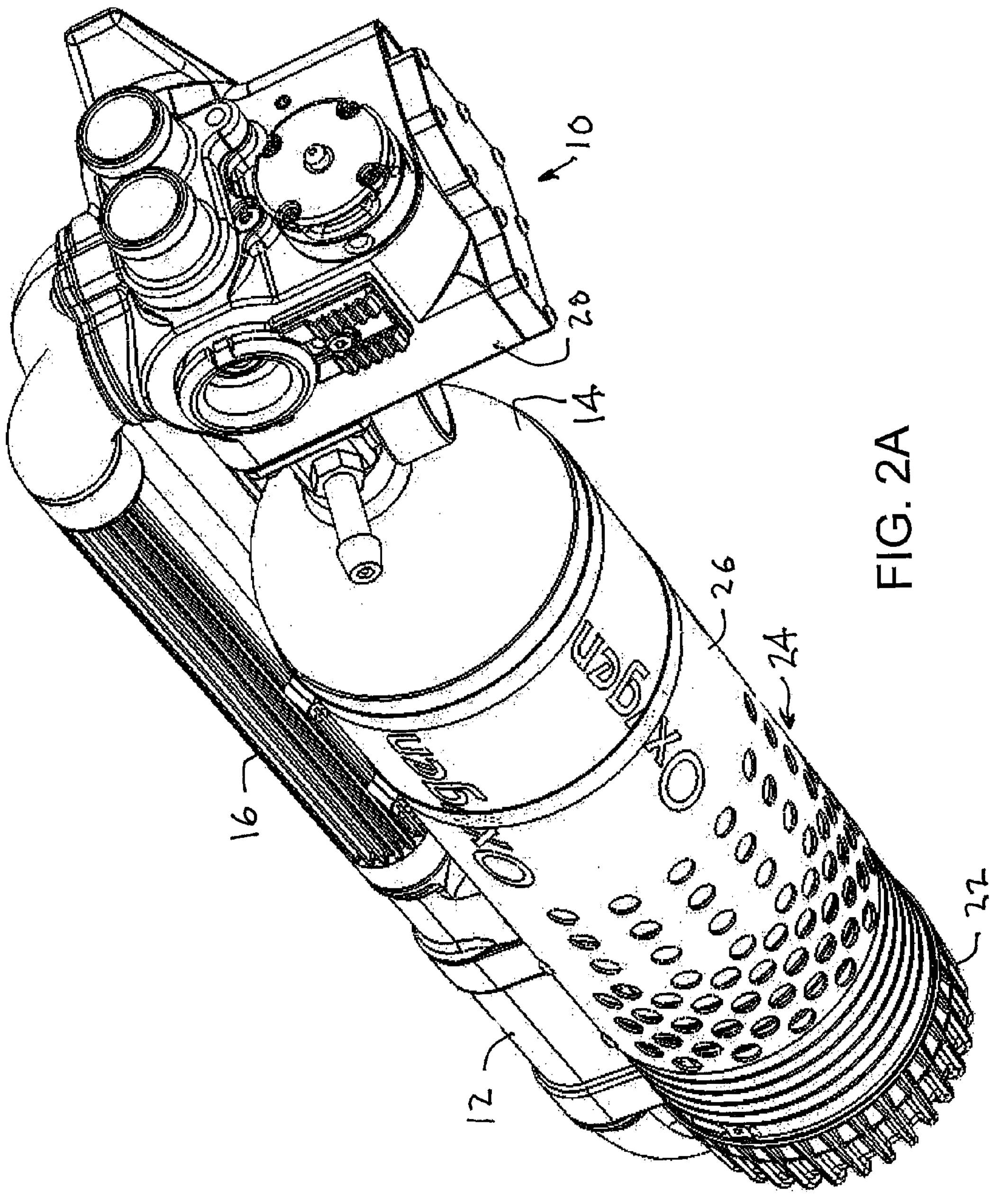
FIG. 2A illustrates an aircrew rebreather system that is in accordance with the present invention.
Figure 2B:
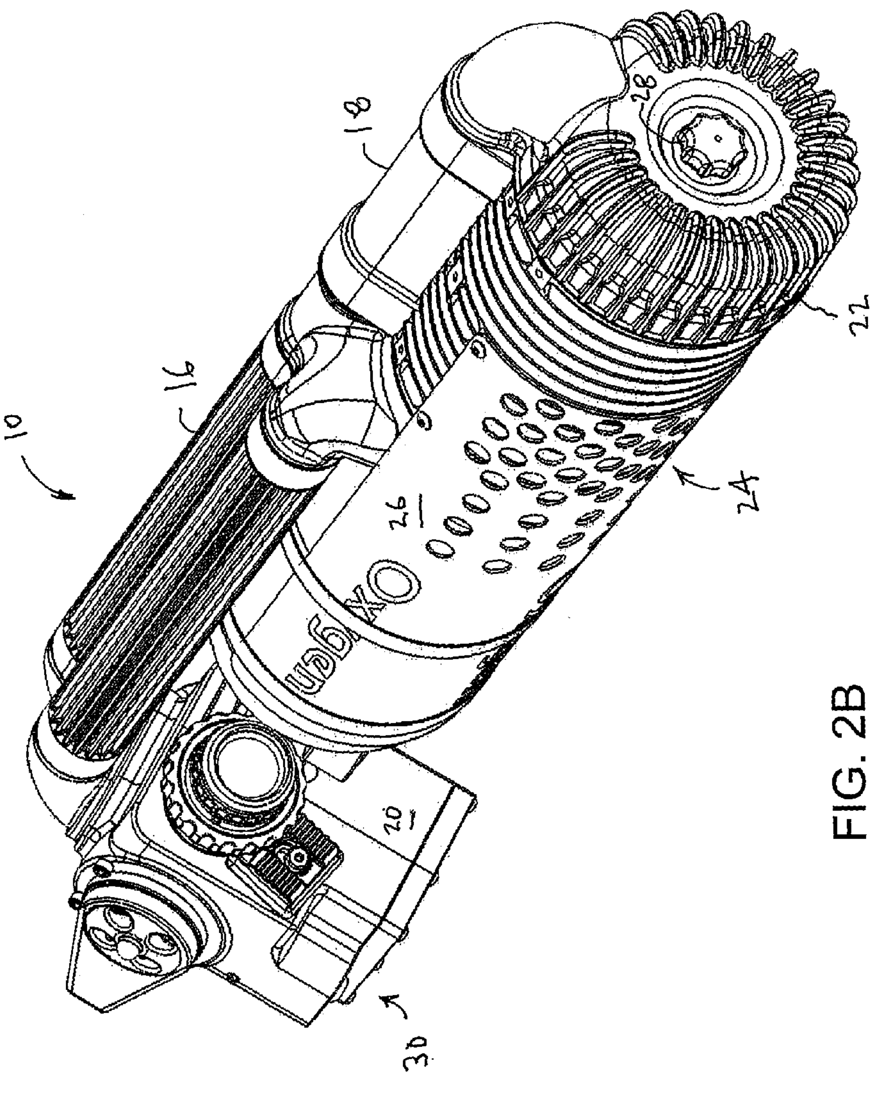
FIG. 2B is an alternate view of the rebreather system shown in FIG. 1.

Referring now to the drawings, there is illustrated in FIGS. 2A and 2B a rebreather system 10 that allows for open circuit as well as closed circuit breathing modes and dramatically extends the useable oxygen time compared to the current system (in closed circuit mode (note comparison in following pages)). Pressure breathing boost is controlled automatically. The monitoring electronics activates (turns on/off) automatically with the control barrel position.

The rebreather system 10 incorporates a solid state highly optimized scrubber system 12 in-line with an oxygen tank 14 that is a light-weight carbon fiber based composite. Gas cooling is achieved by a finned extruded aluminum tube 16 which connects a scrubber system to a rebreather head assembly, or control unit, 20 as well as by cooling fins 22 on the scrubber system. The finned tube 16 runs along the side of the oxygen tank 14 parallel to the tank axis. Placing the scrubber system in-line with the oxygen tank allows for streamlining. Additional cooling is provided by a plurality of apertures 24 provided upon a center section of the scrubber system 18. Positional adjustment of the components is provided by a co-axial alignment sleeve 26 that is disposed over the oxygen tank 14. A scrubber canister disassembly knob 28 allows removable and replacement of the scrubber cartridge. The rest of the system remains assembled which minimizes parts which can get lost or broken. It is possible to remove the scrubber cartridge while the system is in open circuit mode, provided pressure breathing is not required.

The system 10 is modular so that it can fit multiple missions. This modularity is achieved by the in-line design. If more duration is required a larger tank can be fitted, or the present tank could be pumped to a higher pressure. Use of a larger tank will require only the gas tube and the center section of the scrubber to be changed to components with a greater length. If less weight is desired then these same components can be changed with shorter, and therefore lighter, components. As shown, the system 10 packages in nearly the identical envelope as the prior art systems and weighs less than 10 lbs.

Figure 3:
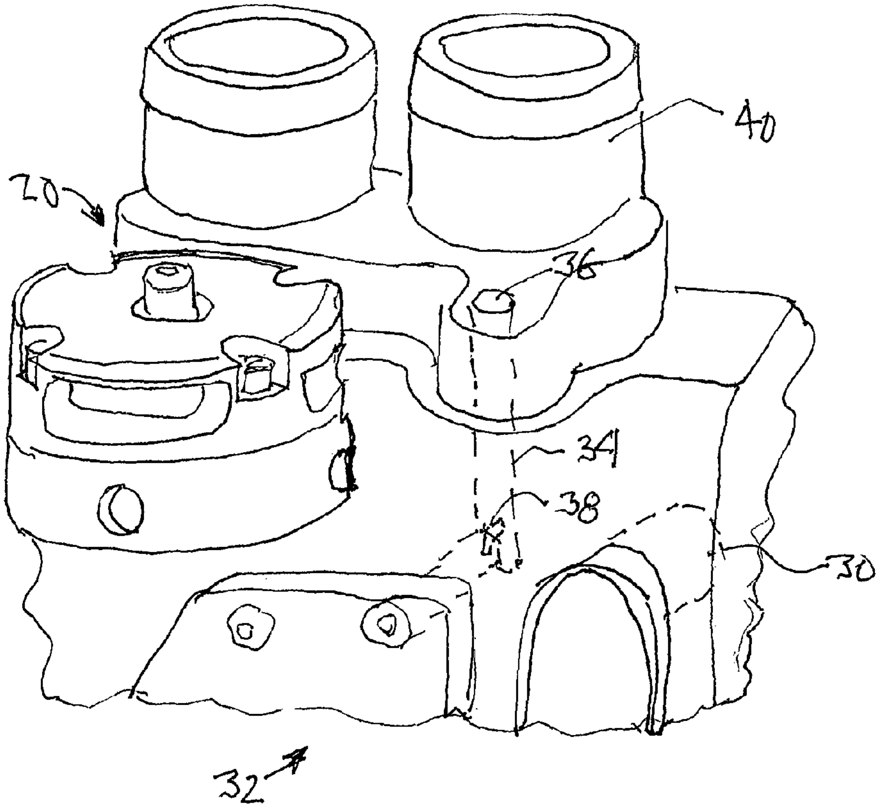
FIG. 3 illustrates components contained within the head assembly of the rebreather system shown in FIG. 1.
Figure 21:
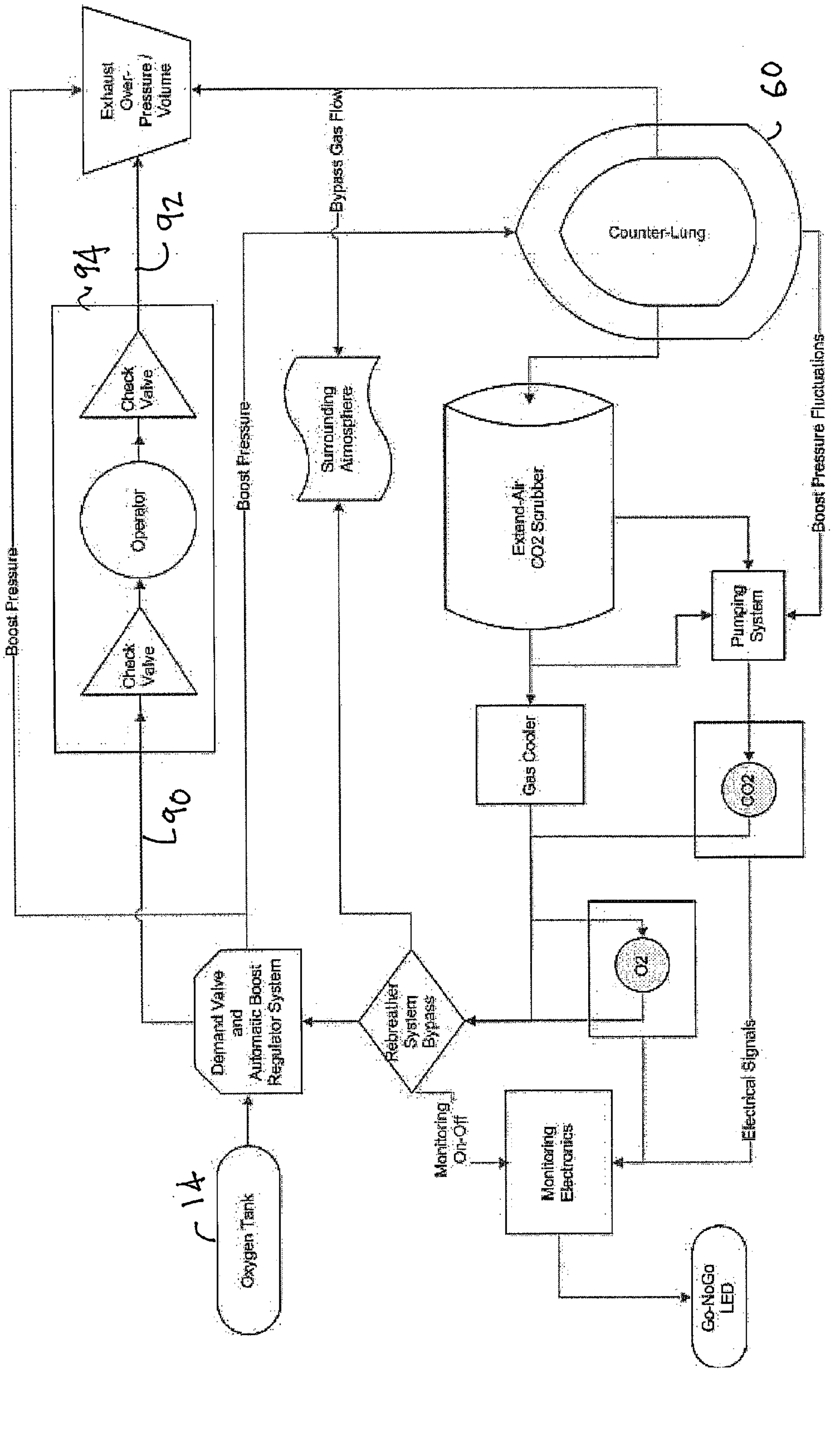
FIG. 21 is a flow chart that illustrates the operation of the rebreather system shown in FIG. 1.

The scrubber 12 utilizes a solid state scrubber media that will not settle and will not create dust. The solid state media is also easier to remove and replace opposed to repacking with granules. The system 10 also includes batteries 30 that are external to the breathing loop as are the electronics. This removes a potential ignition source from an oxygen rich environment. As best seen in FIG. 3, both the batteries 30 and gas monitoring electronics 32 are sealed from the surrounding atmosphere. A system which will be used to inform the operator of system status will be purely fiber optic. A bi-color LED (light emitting diode) 34 is be potted into the rebreather head 20, thus sealing it. This LED will shine up a fiber optic tube (not shown) to a point on an operator's mask (not shown) within visual reference. An aperture 36 for receiving the fiber optic tube is shown in FIG. 3. The monitoring system is turned on and off via a magnetic reed switch 38. The magnetic reed switch will also be potted into the rebreather head assembly 20. Also illustrated in FIG. 3 is a dual hose disconnect 40 with inlet and outlet ports for connecting a pair of breathing hoses 90 and 92 to a conventional operator's mask 94 as shown in FIG. 21. The system 10 further includes a counterlung 60 that will be described in detail below and is illustrated in FIGS. 9 through 12.

The system 10 could be used by aircrew for HALO (High Altitude Low Opening) or HAHO (High Altitude High Opening) operations into hostile areas. The fact that the system is sealed would also allow a combat swimmer to parachute in and then swim underwater to the target, perform the mission and then swim back out to be picked up by another team. This one system could replace two and save weight and expense. Two systems ganged together could provide up to 4 hours of duration at a total weight of approximately 20 lbs. Because the system is modular it is possible to tailor the system as needed. Simply filling the same size oxygen tank to 2000 psi and lengthening the scrubber cartridge by two inches would also allow for approximately 4 hours of duration as well, depending on work load and metabolic oxygen consumption. This would only add approximately 2 lbs for a total system weight less than 12 lbs.

Figures 13A, 13B, 13C, 13D, 13E, 13F:
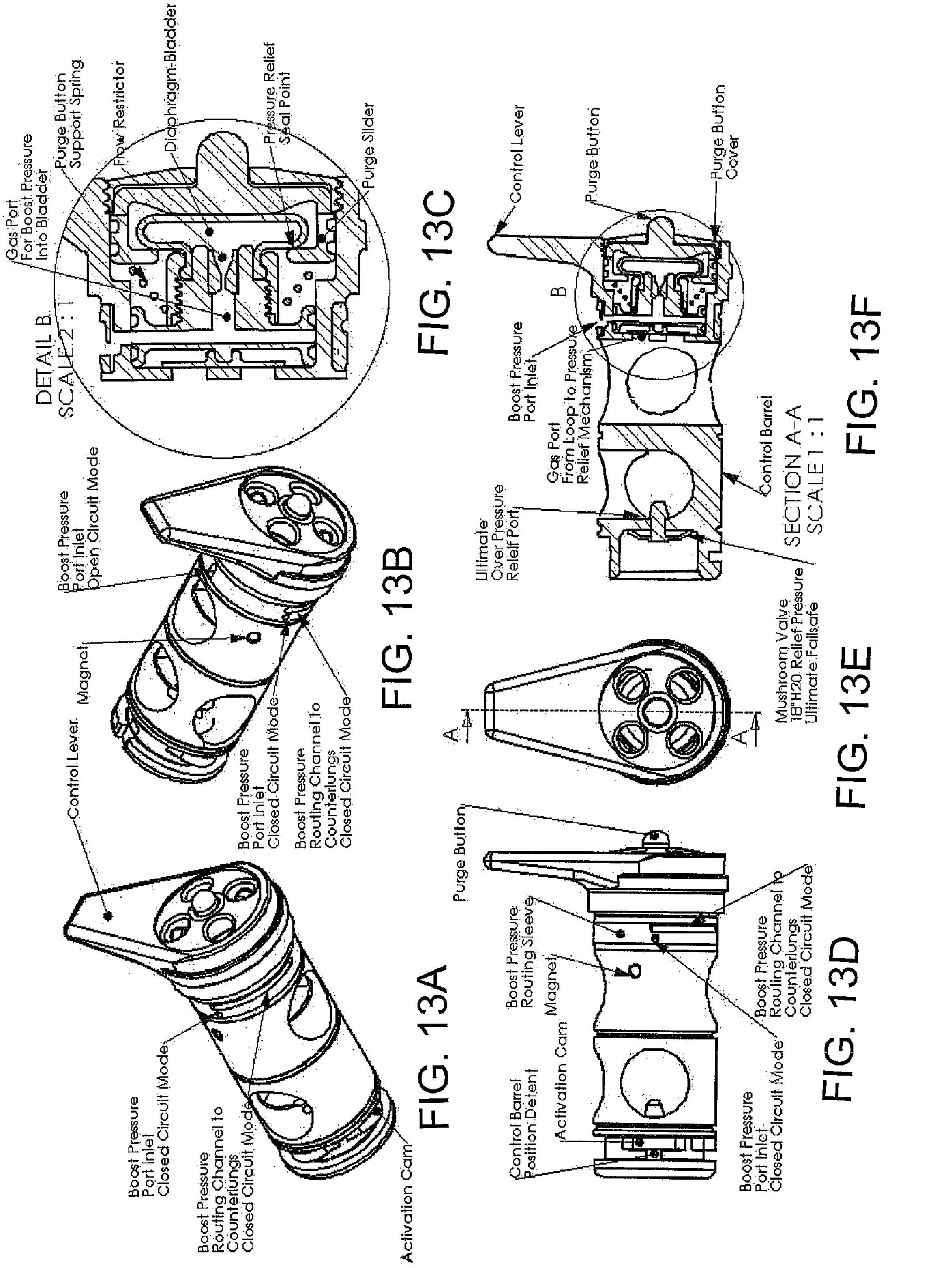
FIG. 13A illustrates is a first perspective view of an valve mechanism that is included in the rebreather system shown in FIG. 1.
FIG. 13B is a second perspective view of the valve mechanism that is included in the rebreather system shown in FIG. 1.
FIG. 13C is an enlarged view of a portion of FIG. 13F.
FIG. 13D is a side view of the valve mechanism shown in FIG. 13A.
FIG. 13E is a end view of the valve mechanism shown in FIG. 13A.
FIG. 13F is a sectional view of the valve mechanism in shown FIG. 13A taken along line A-A in FIG. 13E.
Figure 14D:
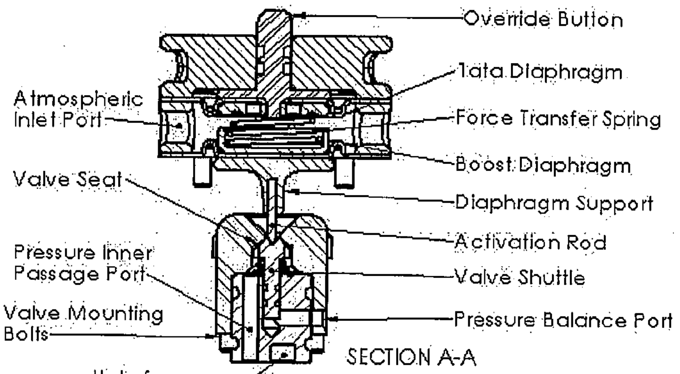
FIG. 14D is a sectional view of the balanced demand valve shown in FIG. 14A taken along line A-A in FIG. 14C.
Figure 14C:
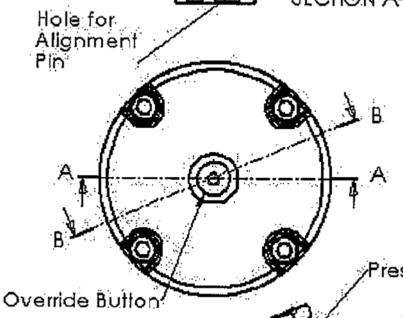
FIG. 14C is an end view of the balanced demand valve shown in FIG. 14A.
Figure 14B:
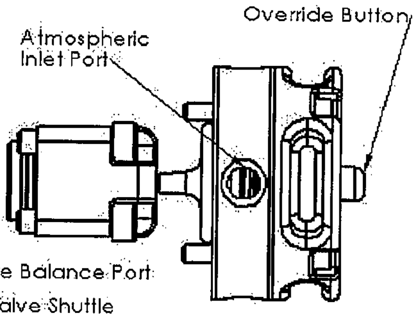
FIG. 14B is a side view of the balanced demand valve shown in FIG. 14A.
Figure 14E:
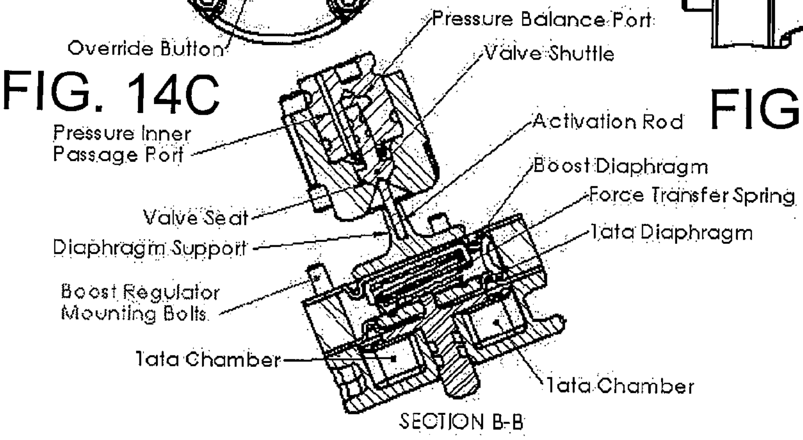
FIG. 14E is a sectional view of the balanced demand valve shown in FIG. 14A taken along line B-B in FIG. 14C.
Figure 14A:
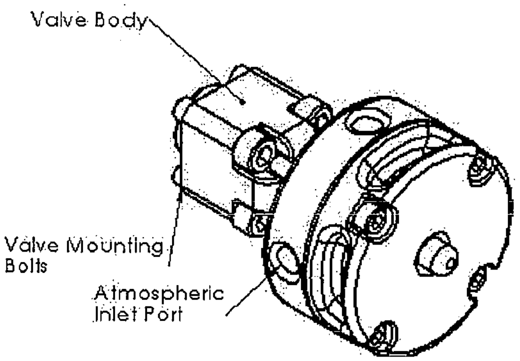
FIG. 14A is a perspective view of a balanced demand valve regulator that is included in the rebreather system shown in FIG. 1.
Figures 15A, 15B, 15C, 15D:
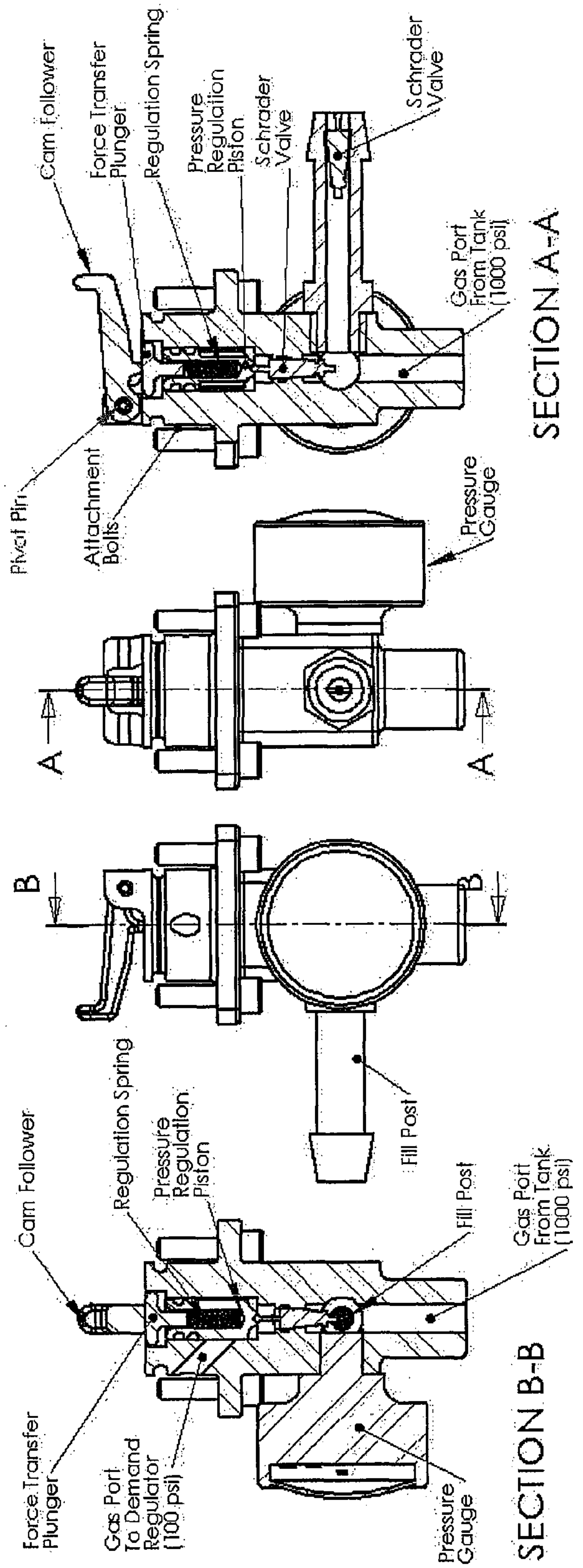
FIG. 15A is a front view of a first stage pressure regulator system that is included in the rebreather system shown in FIG. 1.
FIG. 15B is a side view of the first stage pressure regulator system that is shown in FIG. 15A.
FIG. 15C is a sectional view of the first stage pressure regulator system that is shown in FIG. 15A taken along line B-B in FIG. 15A.
FIG. 15D is a sectional view of the first stage pressure regulator system that is shown in FIG. 15A taken along line A-A in FIG. 15B.
Figures 16A, 16B, 16C, 16D, 16E, 16F:
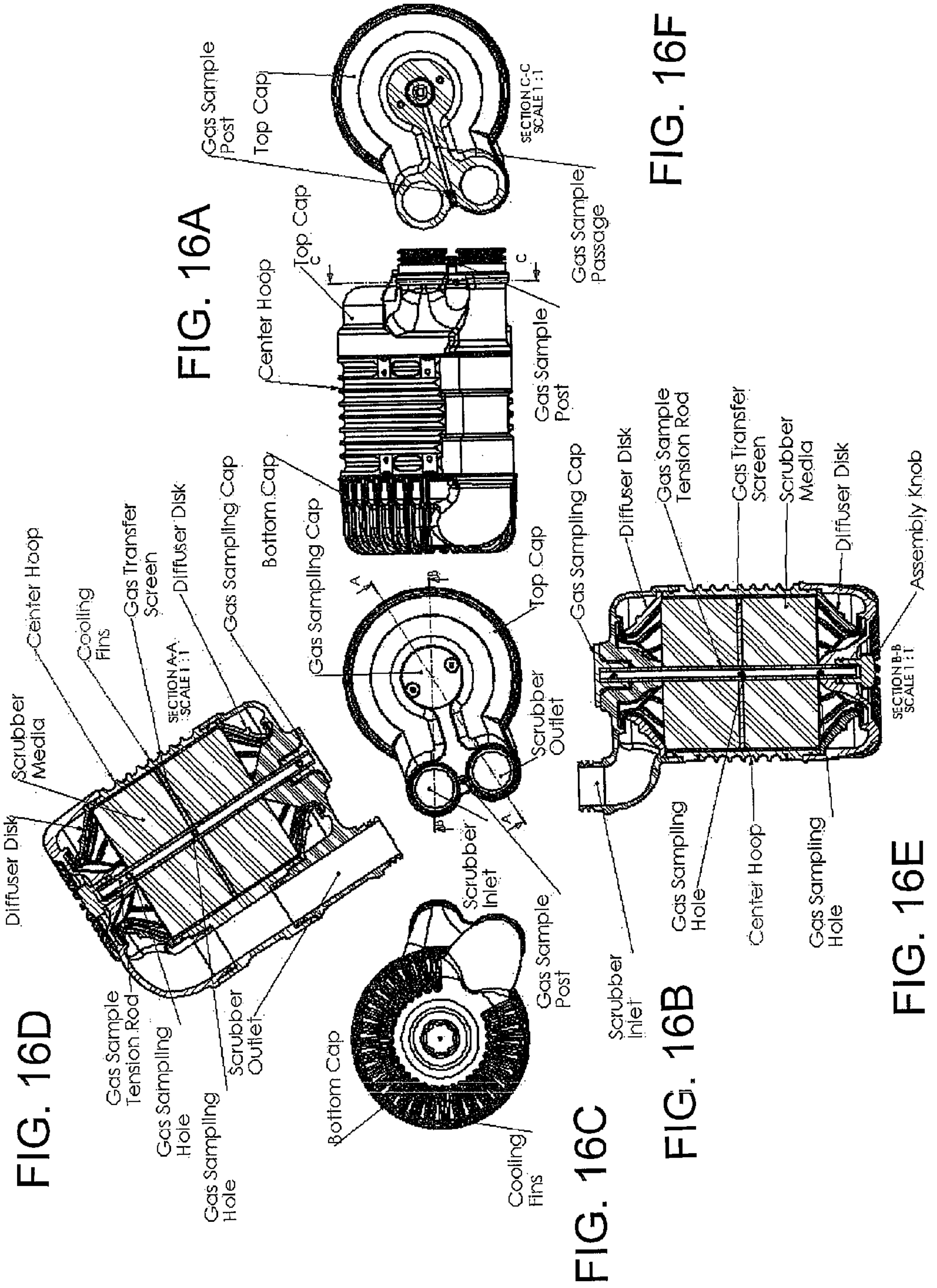
FIG. 16A is a side view of a gas scrubber system that is included in the rebreather system shown in FIG. 1.
FIG. 16B is a top view of the gas scrubber system shown in FIG. 16A.
FIG. 16C is a bottom view of the gas scrubber system shown in FIG. 16A.
FIG. 16D is a sectional view of the gas scrubber system shown in FIG. 16A taken along line A-A in FIG. 16B.
FIG. 16E is a sectional view of the gas scrubber system shown in FIG. 16A taken along line B-B in FIG. 16B.
FIG. 16F is a sectional view of the gas scrubber system shown in FIG. 16A taken along line C-C in FIG. 16A.
Figures 18A, 18B, 18C, 18D, 18E, 18F, 18G:
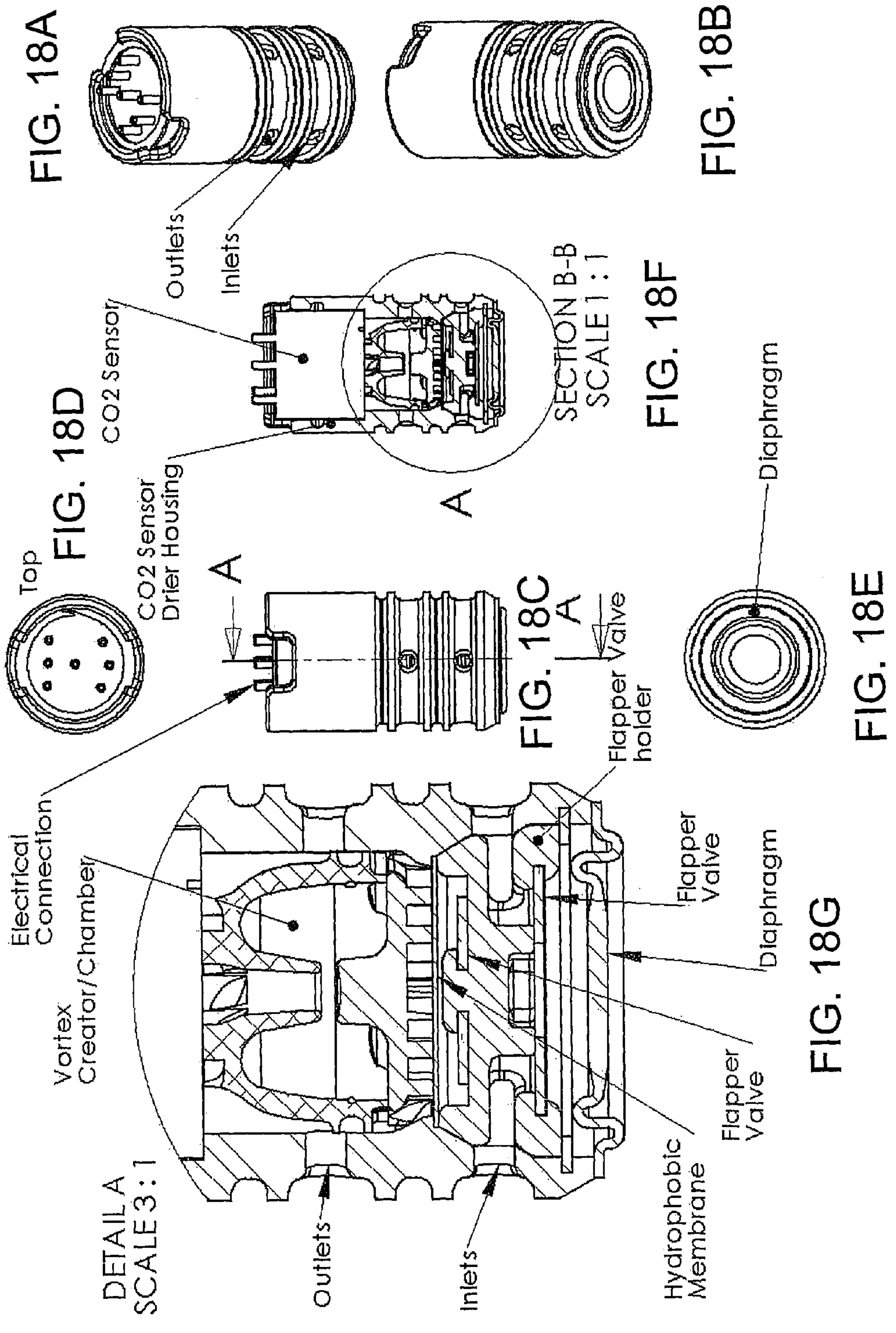
FIG. 18A is a perspective view taken from above a gas drying system that is included in the rebreather system shown in FIG. 1.
FIG. 18B is a perspective view taken from below a gas drying system that is included in the rebreather system shown in FIG. 1.
FIG. 18C is front view of the gas drying system shown in FIGS. 18A and 18B.
FIG. 18D is top view of the gas drying system shown in FIG. 18C.
FIG. 18E is bottom view of the gas drying system shown in FIG. 18C
FIG. 18F is sectional view of the gas drying system shown in FIG. 18C that is taken along line A-A.
FIG. 18G is an enlarged view of a portion of the gas drying system shown in FIG. 18F.
Figures 19A, 19B, 19C, 19D, 19E, 19F, 19G:
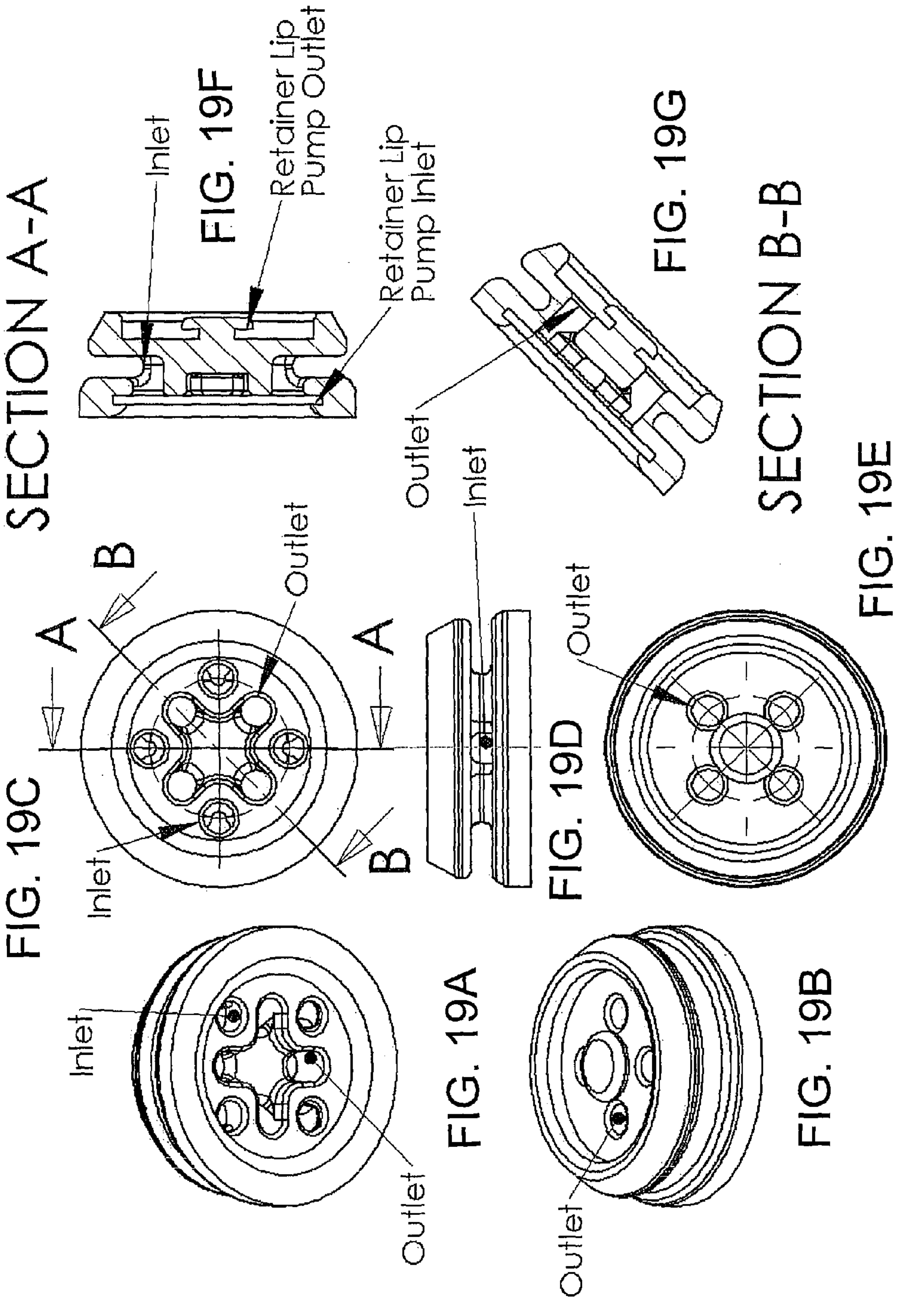
FIG. 19A is a perspective view taken from above of flow ports of a pumping system that is included in the gas drying system shown in FIGS. 18*a* through 18G.
FIG. 19B is a perspective view taken from below of the flow ports shown in FIG. 19A.
FIG. 19C is a top view of the flow ports shown in FIG. 19A.
FIG. 19D is a side view of the flow ports shown in FIG. 19A.
FIG. 19E is a bottom view of the flow ports shown in FIG. 19A.
FIG. 19F is a sectional view of the flow ports shown in FIG. 19A taken along line A-A in FIG. 19C.
FIG. 19G is a sectional view of the flow ports shown in FIG. 19A taken along line B-B in FIG. 19C.
Figure 20A:
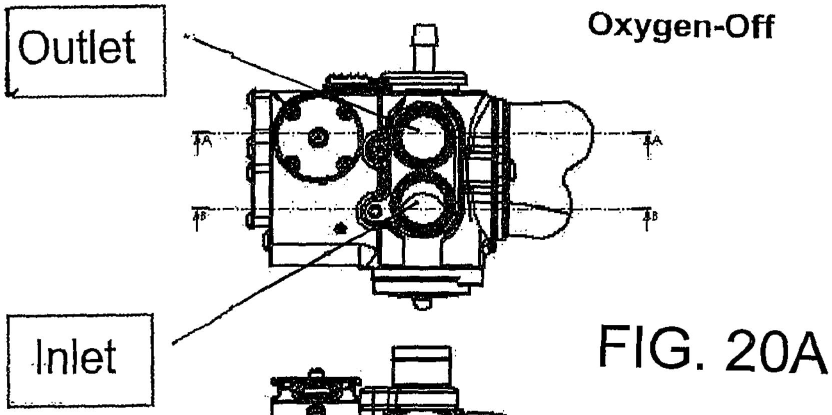
FIG. 20A is a top view of the head assembly shown in FIG. 4A with the operating lever placed in an oxygen-off mode position.
Figure 20B:
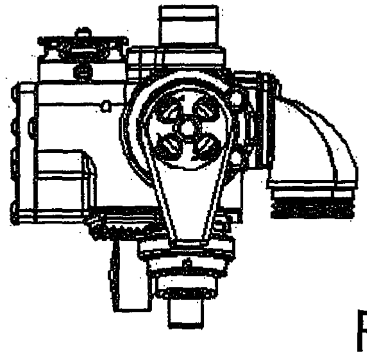
FIG. 20B is a side view of the head assembly shown in FIG. 20A.
Figure 20C:
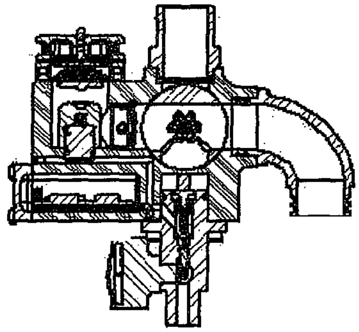
FIG. 20C is a sectional view of side view of the head assembly shown in FIG. 20A taken along line A-A.
Figure 20D:
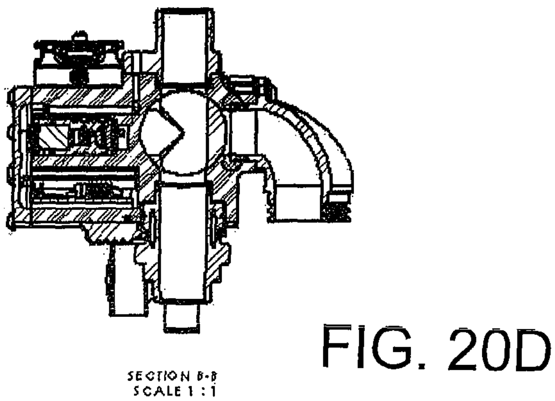
FIG. 20D is a sectional view of side view of the head assembly shown in FIG. 20A taken along line B-B.
Figure 20E:
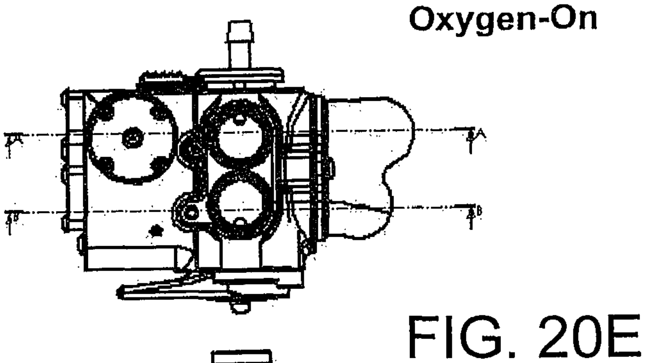
FIG. 20E is a top view of the head assembly shown in FIG. 4A with the operating lever placed in an oxygen-on/open circuit mode position.
Figure 20F:
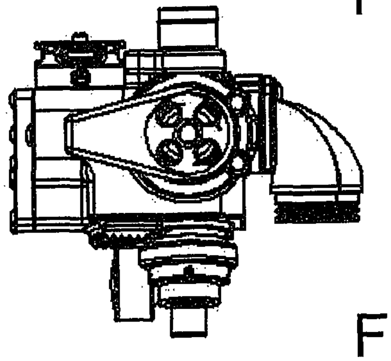
FIG. 20F is a side view of the head assembly shown in FIG. 20E.
Figure 20G:
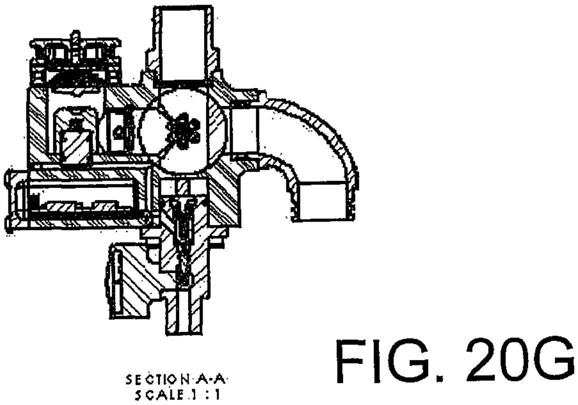
FIG. 20G is a sectional view of side view of the head assembly shown in FIG. 20E taken along line A-A.
Figure 20H:
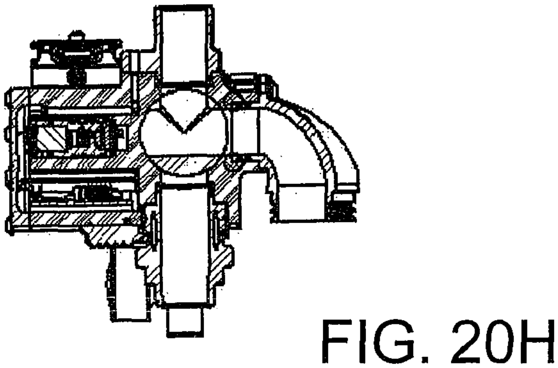
FIG. 20H is a sectional view of side view of the head assembly shown in FIG. 20E taken along line B-B.
Figure 20I:
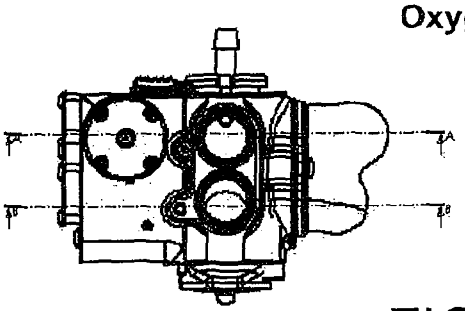
FIG. 20I is a top view of the head assembly shown in FIG. 4A with the operating lever placed in an oxygen-on/closed circuit mode position.
Figure 20J:
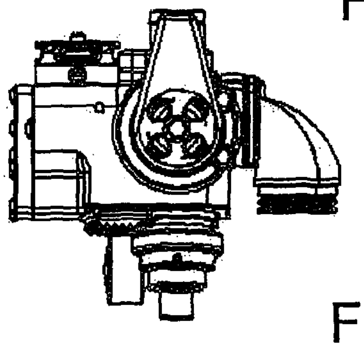
FIG. 20J is a side view of the head assembly shown in FIG. 20I.
Figure 20K:
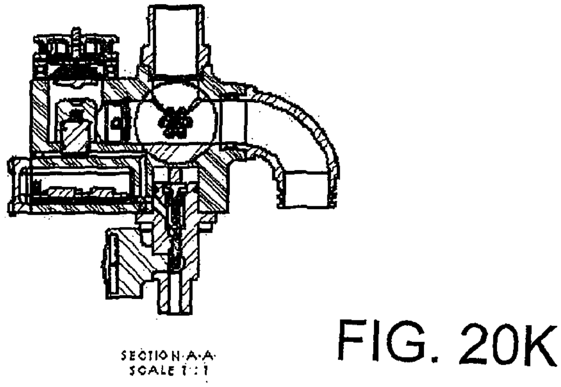
FIG. 20K is a sectional view of side view of the head assembly shown in FIG. 20I taken along line A-A.
Figure 20L:
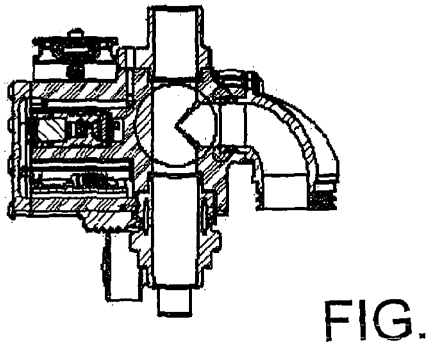
FIG. 20L is a sectional view of side view of the head assembly shown in FIG. 20I taken along line B-B.

FIGS. 4A through 4F illustrate a number of details of the rebreather system head assembly 20 with individual components identified with labels. While the header assembly 20 is very tightly packaged, it may be possible to further reduce the footprint of the rectangular silhouette by moving the Pressure Boost System and Electronics to the opposite side of the Control Barrel Lever, or simply the control lever, 42 above the Fill Post. A metered leak to make this a semi-closed rebreather system could also be placed between the inlet/outlet ports and the pressure boost system shown in FIGS. 4A through 4F and as illustrated in FIG. 13C. It is noted that all of the gas passageways are internal to the rebreather head assembly 20. This means that there are few items may be damaged by contact with other devices. Various cross-sectional views of the rebreather head assembly are shown in FIGS. 5A through 5D, where the individual components are again identified with labels. The rebreater head assembly 20 includes a Pressure Relief System that incorporates a flow restrictor in the throat of a Diaphragm-Bladder. The location of the Magnet used to turn on/off the electronics corresponds to the electronics location. There also is a Sleeve which routes the pressure from the boost chamber to the counterlungs, that is, the space between the two bags, as well as at the Pressure Relief System. Boost pressure routing changes with the position selected for the control lever 42.

The present invention contemplates achieves a number of objectives, namely:

Objective 1: Pressure Breathing With a Rebreather System;
Objective 2: Strategy for Robust Breathing Loop Control;
Objective 3: $CO_2$ Scrubber Status Determination;
Objective 4: Packaging of Solution and User Interface; and
Objective 5: Modify $PPO_2$ Controller for Altitude Use Regarding Objective 1, pressure breathing is required in breathing apparatus for flight ceilings above 43000 ft. in order to prevent the risks of hypoxia. Several prior art land based systems use pressure breathing mechanisms, via springs on the counterlungs. The need for a variable boost, which changes with altitude, was investigated. This also required the venting pressure to be variable corresponding to the boost pressure.

Rebreathers in general are complex systems made up of interconnected and interdependent subsystems frequently with overlapping purposes. Designing a rebreather for pressure breathing requires three separate systems to work synergistically, namely:

1. A Counterlung System;
2. An Over-Pressure Relief (Over-Volume Venting) System; and
3. A Balanced Demand Valve Regulator.

Additionally, all three systems must be counterbalanced with the boost pressure.

There are limits on how much pressure can be exerted on alveolar tissues before damage occurs. Even low boost pressures can create discomfort for the operator. Boosted inhalation pressure is complicated by higher exhalation pressures. This results in an overall increase in work of breathing (WOB). This can not only fatigue the operator but it can also result in a build up of $CO_2$ within the breathing mask.

Regarding the counterlung system, Matlab Simulink was utilized as a primary tool to model the breathing loop, operator and control mechanism of the rebreather system 10. The inventor used this tool to gauge the effects of using an elastic bladder system for the pressure breathing mechanism to that of a fixed sealed outer enclosure. What was predicted from simulation was that the elastic bladder would produce substantially smaller pressure variations than the sealed enclosure of the same size. The inventor modeled several systems.

Method 1—

Figure 6:
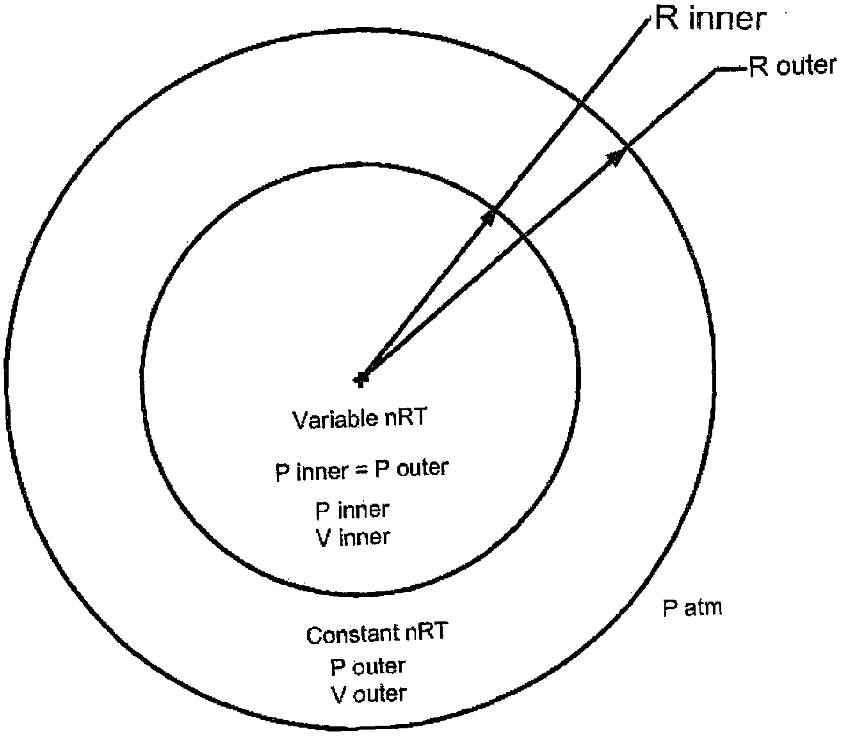
FIG. 6 shows a first model for analyzing a counterlung configuration for the rebreather system shown in FIG. 1.

Mounting a counterlung inside a box that can be pressurized. From mathematical modeling it was found that using this method created widely varying pressure inside the counterlung, breathing loop and operator lungs. Our initial assumptions that this method would not work within a small envelope were confirmed by simulation. We modeled this as an air-tight sphere (which was totally elastic ie. No resistance to size change) within an air-tight rigid outer sphere. The number of gas moles between the inner and outer sphere was kept constant. FIG. 6 is a graphical representation of this approach. The model was implemented into a simulation using Matlab Simulink.

Method 2—

Figure 7:
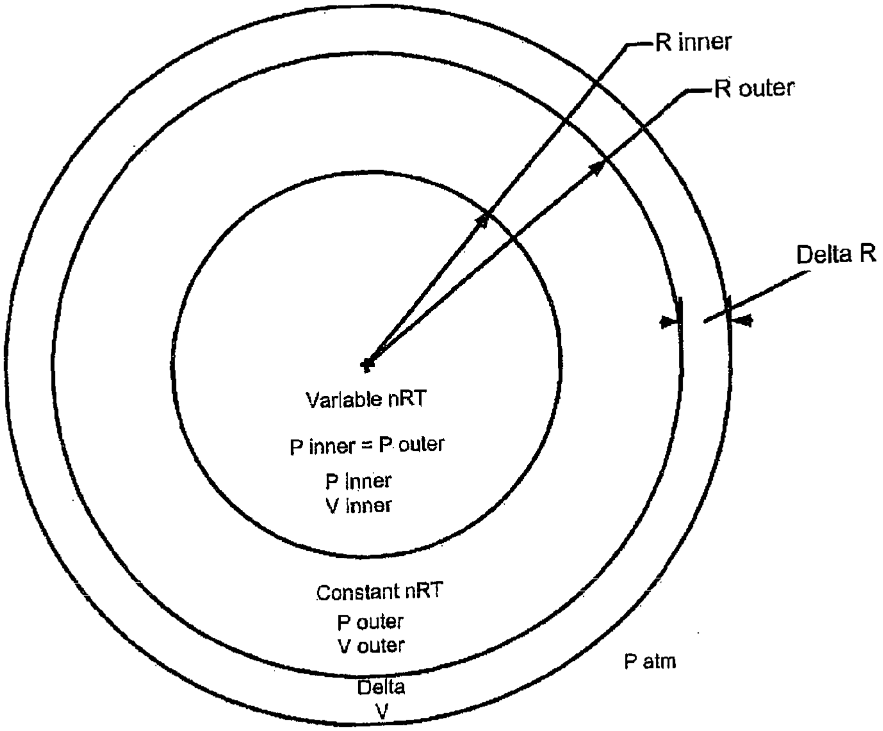
FIG. 7 shows a second model for analyzing a counterlung configuration for the rebreather system shown in FIG. 1.

Mounting the counterlung inside an elastic membrane where the space between the counterlung and membrane can be pressurized. This method appears to provide an effective solution as noted in FIG. 7. The gas pressure on the outside of the counterlung still fluctuates with operator inhale/exhale cycles but it is more constant over the breathing cycle as compared to method #1. For simulation purposes, the inventor modeled the counterlung system of method #2 as two spherical bags, one inside the other with boost pressure being applied to the volume between the two bags. The outer bag was given an elastic spring constant (K). Boost pressure fluctuated with the operators breath. It is modeled as the Variable nRT for the inner volume. For simplicity assume that the normal force (F) on the bag varies with the square of the change in radius (Δr) or the outer sphere $$F=K\Delta r^2 \qquad \text{Eqn. 1}$$

Determine the Pressure difference $P_{delta}$ $$P_{delta}=(P_{outer}-P_{atm}) \qquad \text{Eqn. 2}$$

Given (P is pressure, F is force and A is area)

$$P=\frac{F}{A} \qquad \text{Eqn. 3}$$

The force is from the stretch of the outer bag. The area is the spherical surface area.

$$P_{delta}=\left(\frac{K\Delta r^2}{4\Pi r_{outer}^2}\right) \qquad \text{Eqn. 4}$$

Solve for the change in radius $$\Delta r=\sqrt{\frac{(P_{outer}-P_{atm})\Pi r_{outer}^2}{K}} \qquad \text{Eqn. 5}$$

From Ideal gas law find the dynamic volume in the inner bag. (P is pressure, V is volume, n is the number of moles, R is the gas constant, T is temperature)

$$P_{outer}V_{outer}=nRT\ \text{Constant} \qquad \text{Eqn. 6}$$

$$P_{inner}V_{inner}=nRT\ \text{Varied} \qquad \text{Eqn. 7}$$

$$V_{inner}=\frac{V_{outer}n_{inner}}{n_{outer}} \qquad \text{Eqn. 8}$$

$$V_{inner}=\frac{\frac{4}{3}\Pi(R_{outer}+\Delta r)^3 n_{inner}}{n_{outer}} \qquad \text{Eqn. 9}$$

Substituting:

$$V_{inner}=\left[\frac{\frac{4}{3}\Pi\left(r_{outer}+\sqrt{\frac{(P_{outer}-P_{atm})\Pi r_{outer}^2}{K}}\right)^3 n_{inner}}{n_{outer}}\right] \qquad \text{Eqn. 10}$$

This math was implemented into a simulation using Matlab Simulink.

Figure 8:
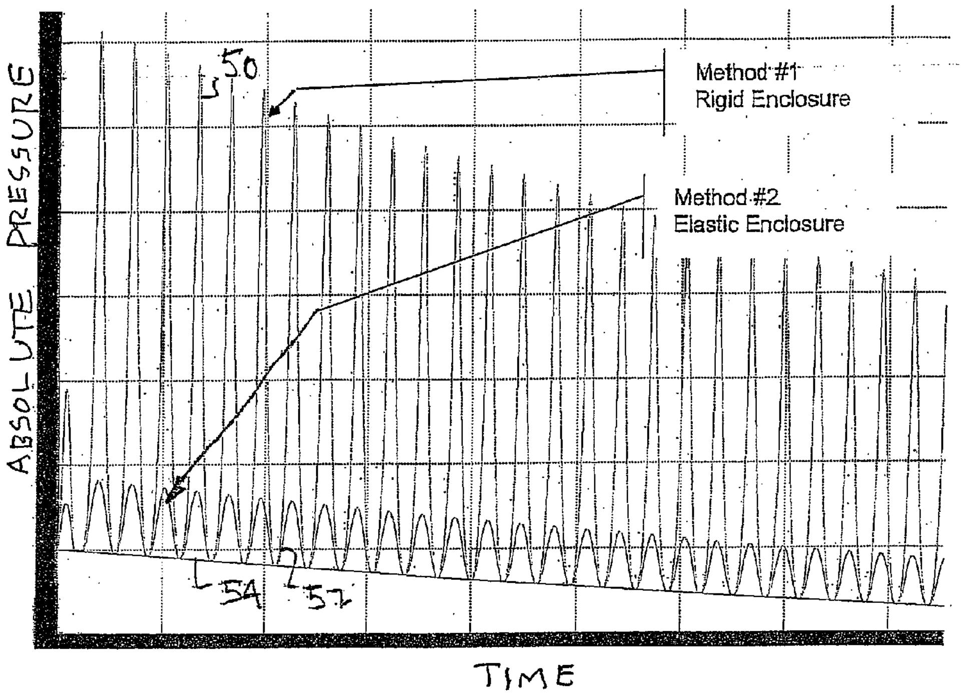
FIG. 8 illustrates the results obtained from models shown in FIGS. 6 and 7.

Both Simulink models were solved simultaneously. Solving for $P_{delta}$ results in the following; the pressure variation of the elastic enclosure is approximately 4 times smaller on average. FIG. 8 details the pressure variation over time. The pressure on the left side is in inches $H_2O$ (0.5-4) the bottom scale is in seconds (0-155). The vertical axis is the absolute pressure, the horizontal axis is time. The signal labeled 50 is from the rigid enclosure, the signal labeled 52 is from the elastic enclosure. The line labeled 54 is the ambient pressure.

Figure 9:
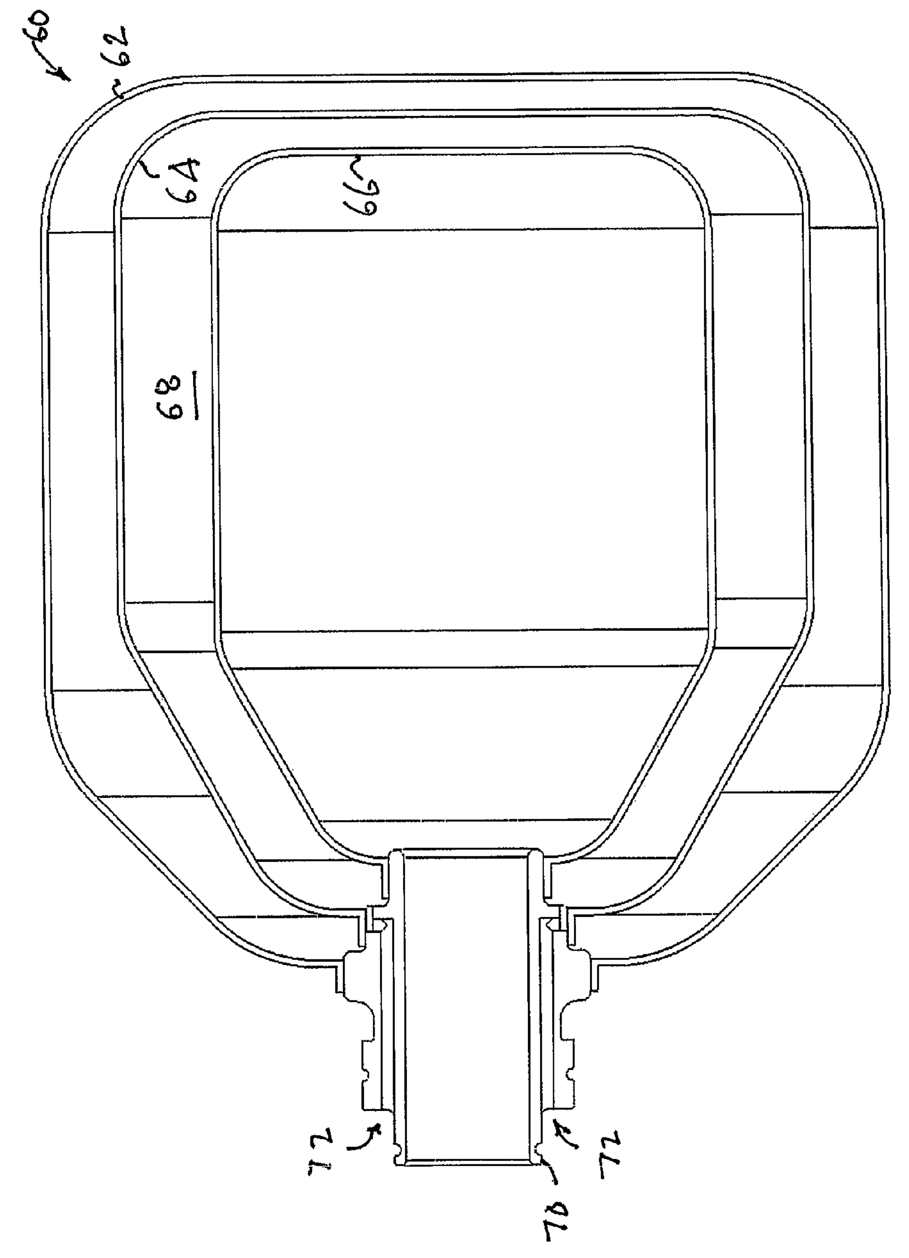
FIG. 9 illustrates a double bagged gas storage bladder system, or counterlung, for use with rebreather system shown in FIG. 1.
Figure 10:
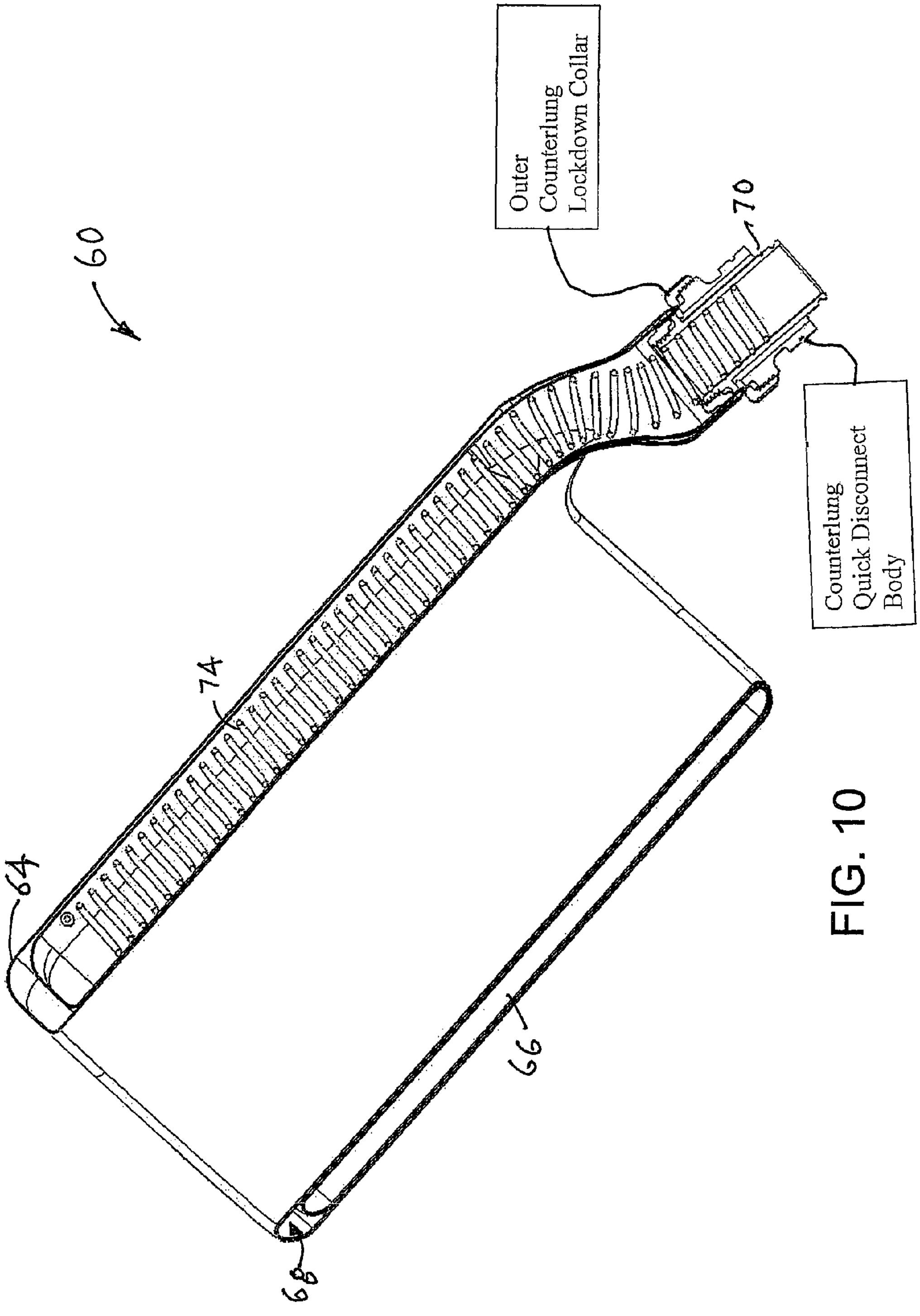
FIG. 10 is a sectional view of the counterlung utilized with the rebreather system shown in FIG. 1.
Figure 11:
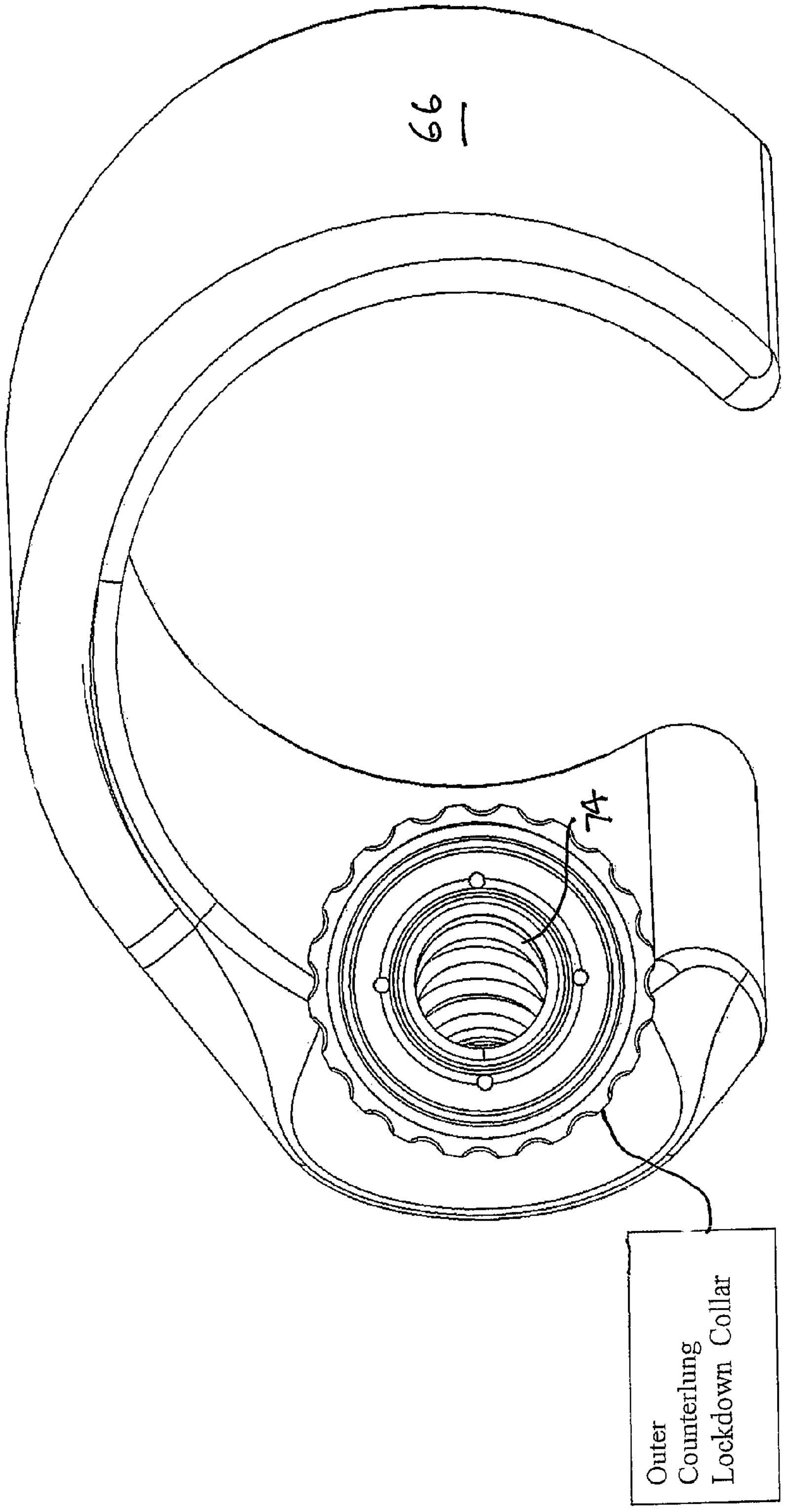
FIG. 11 is an end view of the counterlung shown in FIG. 10.
Figure 12:
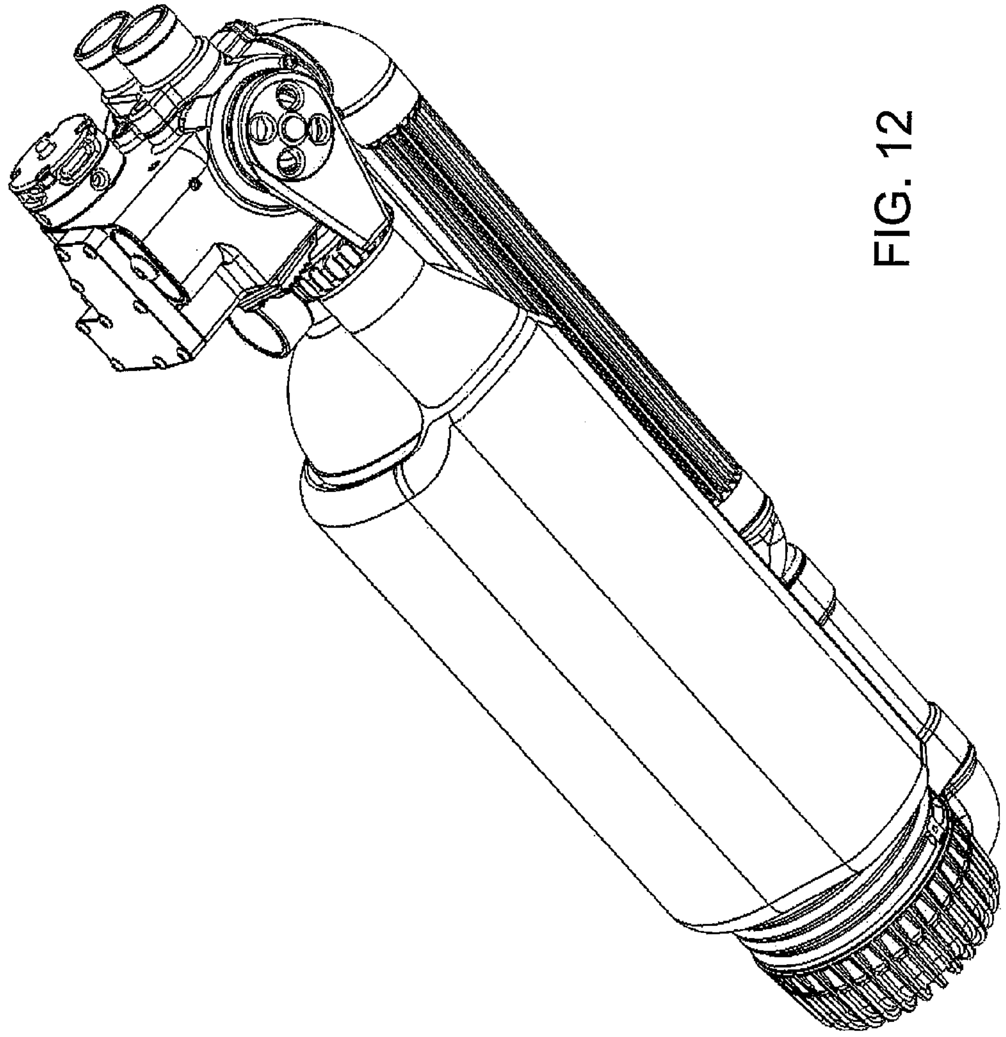
FIG. 12 isslustrates the counterlung shown in FIG. 10 installed upon the rebreather system shown in FIG. 1.

From the above, it is clear that the proper functioning of the counterlung is pivotal to these other systems working correctly. A double bagged gas storage bladder system, or counterlung, 60 is perhaps the single most important mechanism of the rebreather system 10. The counterlung arrangement utilized in the present invention is illustrated in FIG. 9. The counterlung 60 includes an non-elastic, or rigid, outermost layer 62 that is simply an outer protective cover which will be designed to simply help to hold and locate the counterlung on the oxygen supply tank 14. Within the outer layer 62 is an outer elastic counterlung membrane 64 that encloses a non-elastic inner counterlung membrane 66. A void 68 is defined between the outer and inner counterlung membranes 64 and 66 that may be pressurized to boost pressure. The counterlung components are mounted upon a connector 70 for attachment to the system header assembly 20. Pressure ports 72 extends in an axial direction through the connector to allow pressurization of the void between the counterlung membranes 64 and 66. A sectional view of the counterlung 60 is provided in FIG. 10 that shows an anti-collapse spring 74 that is disposed between the outer and inner counterlung membranes 66 and 68. An end view of the counterlung 60 is shown in FIG. 11 that illustrates that the counterlung is shaped to wrap around the oxygen tank 14 of the rebreather system 10. The installation of the counterlung 60 upon the rebreather system 10 is illustrated by FIG. 12.

The components shown in FIG. 9 are not to relative scale as the outer elastic counterlung will need to be approximately 9 liters while the inner non-elastic counterlung will be approximately 6 liters. The size of the inner counterlung is driven by human physiology while the size of the outer counterlung is driven by overall system performance and size compromises.

Regarding over-pressure relief, on all properly designed rebreather systems there must be a method to vent the breathing loop if it is over-pressurized, which typically happens when the counterlung is too full to allow for respiration. With increasing pressure inside the breathing loop, human lung tissue will fail well before the counterlung or other parts of the rebreather. Accordingly, there must be a vent which cracks open at a pressure relief point that is well below the lung damage point. Some designers of underwater rebreathers have forgotten this point and the divers lungs were proven to be the weak point. The pressure relief point should be set as low as possible without creating leakage during the breathing cycle. The purpose of having the boost pressure balance on this venting mechanism is simply to prevent gas from venting as boost pressure increases. The goal is to allow proper minimal delta pressure over the boost pressure and to allow venting only when appropriate.

Figures 5A, 5B, 5C, 5D:
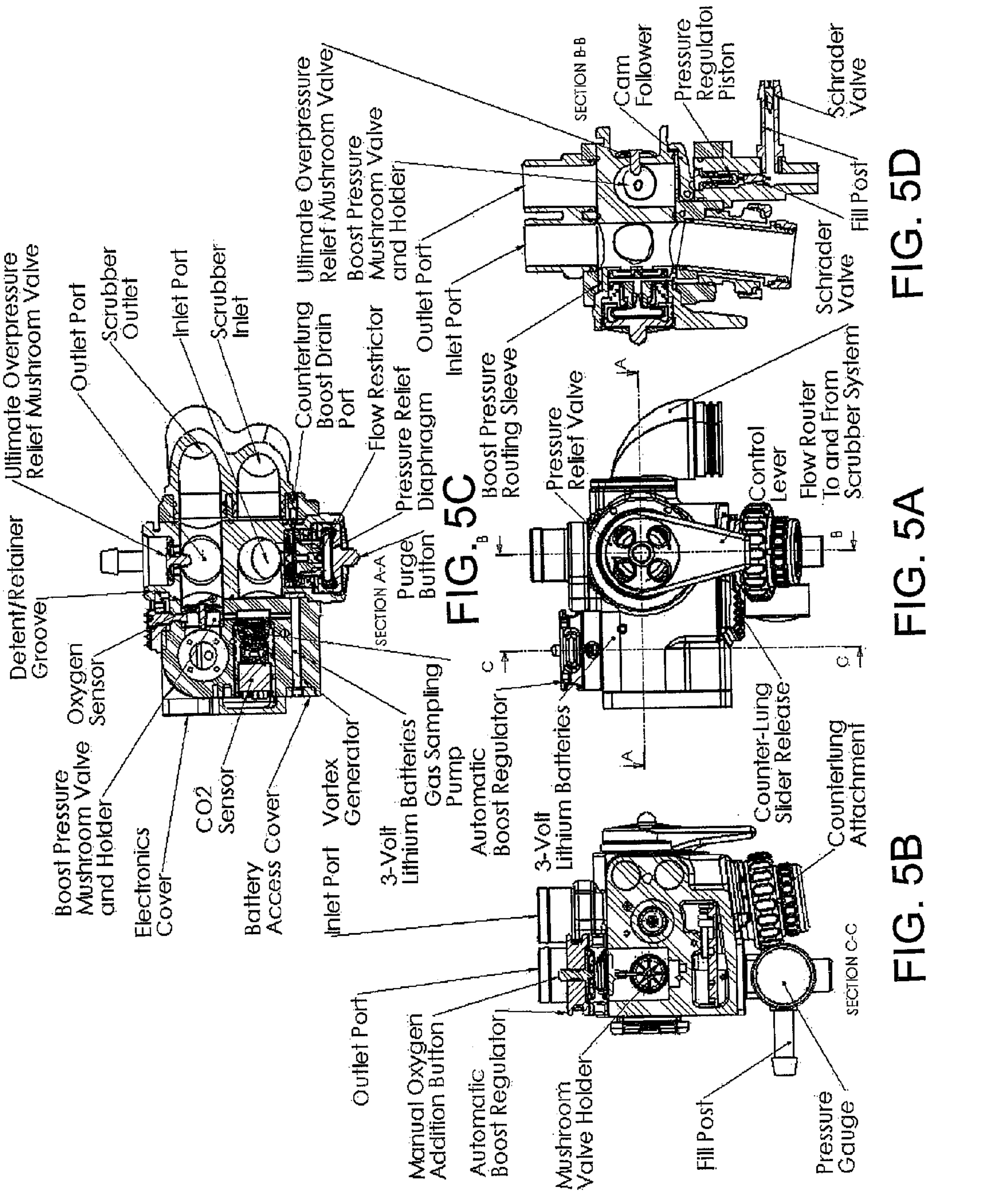
FIG. 5A shows cross sectional view lines of the head assembly shown in FIG. 3.
FIG. 5B is a cross section of the head assembly taken along line C-C in FIG. 5A.
FIG. 5C is a cross section of the head assembly taken along line A-A in FIG. 5A.
FIG. 5D is a cross section of the head assembly taken along line B-B in FIG. 5A.

The present invention incorporates a diaphragm-bladder relief membrane that is illustrated in FIGS. 13A through 13F. It is felt that this design has the best chance for success by minimizing the hysteriesis of the venting operation. An earlier design relied on sliding o-rings. While the initial design would most likely have worked well in laboratory conditions, o-ring seals are prone to leakage and striction in areas where dirt and particulates are present. The goal of the present design change is simply to remove a point of potential failure especially if proper maintenance is not carried out. The diaphragm-bladder as shown in FIG. 13C is expected to be much more robust in the field. Additionally, a flow restrictor is included in the body of the rebreather between the boost chamber and the pressure relief mechanism. There will be pressure variation over the breathing cycle. The mushroom valve, which is located in mushroom valve holder shown in FIG. 5D, is designed to check these variations from entering the boost chamber (The mushroom valve in FIG. 13 is for over-boost relief). The boost chamber will be at or below the pressure found in the breathing loop. It is this difference that is relied on to allow proper venting at the relief diaphragm-bladder. If the mushroom valve fails, the boost in the breathing loop will enter the diaphragm-bladder and prevent the exhaust. By adding a flow restrictor we are essentially adding a filter to slow the response of the diaphragm-bladder system. The venting will occur but at a slightly higher pressure. We have added a mushroom check valve on the outlet side of the control barrel end which is designed to relieve pressure at 18 inches $H_2O$. If there is a leak or a failure in the demand valve, mushroom valve or pressure relief system this will vent gas and prevent damage to the operators' lungs.

Regarding a balanced demand valve regulator, the demand valve to get oxygen into the breathing loop is activated by an in-line rod which is attached to the demand valve diaphragm. One side of that diaphragm is internal to the breathing loop the other side is exposed to atmospheric pressure. If the force on the diaphragm is not balanced with boost pressure, as boost pressure rises in the breathing loop it will cause the diaphragm and activation rod to move away from the regulator piston, which is commonly referred to as valve shuttle) When the rebreather loop has sufficient gas the diaphragm (and activation rod) is balanced away from the demand valve system. As the operator consumes the oxygen from the breathing loop the counterlung will bottom out at the end of the inhale cycle. This bottoming out of the counterlung causes a slight pressure drop in the breathing loop. This pressure drop causes the diaphragm to move and the demand valve to fire adding more oxygen to the breathing loop. In the event that the operator consumes all of the supply gas the overall counterlung volume will gradually reduce and the operator will starve for gas (volumetrically). At no time will the loop go hypoxic.

The valve portion 44 of the present invention is a balanced regulator design that is illustrated in FIGS. 14A through 14E. The activation force remains the same regardless of tank pressure; therefore the demand breathing efforts will remain the same regardless of tank pressure. Activation of the boost pressure is automatic. It is caused by the 1 ata chamber expanding via the 1 ata diaphragm when exposed to ambient pressure less than 1 ata. This relates to the boost pressure by a spring pressing on the Boost Diaphragm. The button protruding to the top is an override button. This is where an emergency breathing pressure mechanism could be added if deemed necessary. In the present invention, the overall volume which is trapped in the 1 ata chamber is significantly reduced from prior art designs, which allows the regulator to be smaller.

With reference to FIGS. 14A through 14E, as the surrounding atmospheric pressure drops with altitude, the trapped volume of air attempts to expand by pushing the upper diaphragm downward. This movement pushes the spring mounted below it. The spring transfers force to the lower diaphragm. The lower diaphragm is attached to the demand valve. The demand valve is located inside the breathing loop and is used to create the boost pressure. The volume between the two diaphragms is connected to atmospheric pressure. Once equilibrium is established between the pressure in the loop and the resulting forces on the lower diaphragm, the system will function as a normal demand valve with a diaphragm operator.

The present invention maintains a minimal baseline boost of about 1-2 inches-$H_2O$ during all operational modes. This is accomplished by preloading the activation arm of the demand valve with tension from the lower diaphragm. Actual pressure boost regulation will occur by the mechanism described above. In order for pressure breathing to function as is typical in prior art walk around systems, the present invention includes built in dead-space for the spring between the upper and lower diaphragms. This allows the upper diaphragm to move with changes in altitude but not necessarily cause an increase in static boost pressure. In order for this design to function correctly, the volume of the 1 ata chamber, the spring length, spring stiffness and dead-space needed to be optimized, which was accomplished with mathematical modeling.

In order to accommodate higher tank pressure, such as, for example, 1000 psi vs. 450 psi, the present invention includes a first stage regulator system to reduce the stress on the Balanced Demand Valve Regulator. The pressure regulator system, which is illustrated in FIGS. 15A through 15D, is quite simple consisting of a plunger, spring, piston and a Schrader valve. As the Cam Follower is activated by the cam on the Control Barrel it causes the Force Transfer Plunger to compress the regulation spring. This spring in turn presses down on the Pressure Regulation Piston which directly acts on the Schrader valve stem. As gas flows through the Schrader valve it builds up pressure on the bottom of the Pressure Regulation Piston which pushes it away from the Schrader valve. Of concern is the flow rate through the Schrader valve. Testing and possible redesign may be needed if this valve does not flow sufficiently for open circuit use only. There are several size options available in these valves but then the force to actuate it may become unmanageably high. The equilibrium point will result in a regulated pressure. An initial target pressure of 100 psi is contemplated. If the tank pressure falls below the regulation pressure, the output pressure will simply be the tank pressure. As the Demand Valve System is pressure balanced, the operator will not notice changes in work of breathing as tank pressure changes until the tank pressure gets below the regulation point of the first stage. This could act as a physical indicator to the operator if he is operating the system in an open circuit mode. The pressure gauge is placed in a position below the valve on the mounting stem for practicality reasons. While this may not place it directly in the operators' sight, depending on unit position, it is the most reasonable place to mount it. From a modularity standpoint it will be easy to screw in a high-pressure hose and run that to a pressure gauge. This option would be needed if applied to HAZMAT and fire-fighting.

Regarding Objective 2, a strategy for a robust breathing loop control, the use of a mixed gas system that required inspired $PPO_2$ (partial pressure of oxygen) to be maintained at 0.21 ata in order to minimize the operators' exposure to oxygen toxicity was considered by the inventor. Also, it was desired to optimize oxygen usage. The thought behind this was if the system had lower partial pressure of oxygen ($PPO_2$) at lower altitudes it would reduce oxygen usage. While this is a valid point for an open circuit system (many are designed to be automatically diluting with atmospheric nitrogen) it is not valid for a closed circuit system. Since all of the gas is recirculated within a closed loop, there is no advantage to using a lower $PPO_2$ with the possible exception of oxygen toxicity. With regards to oxygen conservation our simulation results showed that a mixed gas system actually wasted substantially more oxygen than a closed circuit oxygen rebreather. Most of the gas was wasted on assent. As the operator and rebreather system go from a lower altitude to a higher altitude, the mass fraction of oxygen which was life supporting at the lower altitude would go hypoxic due to the dropping ambient pressure resulting in a lower $PPO_2$. Consequently, the counterlung would inflate due to the lower ambient pressure. Once the counterlung reached maximum volume, every pulse of oxygen which was added, caused a venting of loop volume in order to make room for the injected oxygen. The vented gas contained not only nitrogen but also oxygen. This vented oxygen was then lost to the atmosphere. Closed circuit mixed gas rebreathers require that the gas in the breathing loop be continually monitored and adjusted (either manually or automatically with electronics) in order to maintain life support. One of the greatest dangers of using a mixed gas system for altitude use is the absolute likelihood of an operator breathing down the oxygen level in the breathing loop and then going hypoxic. This danger is very real and a task loaded operator may not be attentive to readouts of his life support system. Secondly, if the electronics fail there would be no warning that the system was not controlling the loop $PPO_2$.

Based upon simulations, it was determined that dangers associated with mixed gas rebreather systems make them unsuited for altitude use by general aircrew personnel. An oxygen rebreather system, as with the present invention, fulfills all of the requirements and does not require any electronics for life support. Not requiring electronics means that a major failure point can be avoided (an electronic controller). Electronics can be added for monitoring purposes but gas addition is purely based on demanded operator breathing volume. Using a pure oxygen rebreather also means that a dilution system is not needed which again reduces complexity and potential for failure. This now means that the gas addition system for both rebreather mode and open circuit mode can be a simple demand valve (diaphragm acting on a levered valve). Since supplemental oxygen systems are by their very nature only needed at altitudes above 10000 ft, oxygen toxicity should not be an issue as ambient pressure is approximately 0.7 ata at 10000 ft. Using 100% oxygen in the breathing loop will result in a $PPO_2$ of 0.7 ata. This oxygen partial pressure level can be breathed almost indefinitely without substantial risk of toxicity and hence there is no need for dilution.

Regarding Objective 3, $CO_2$ scrubber determination, all rebreathers require some mechanism to remove $CO_2$ from the breathing gas before it is rebreathed by the operator. This is typically done in a scrubber bed which is made from chemicals which react with gaseous $CO_2$. These chemicals are typically a calcium or lithium base such as calcium hydroxide or lithium hydroxide. These chemicals precipitate out into calcium carbonate or lithium carbonate respectively when exposed to $CO_2$. As it is a reaction which removes the $CO_2$ from the breathing gas the amount of $CO_2$ which can be scrubbed is directly related to how much scrubber chemical is available in the loop.

Determining the scrubber status is a nontrivial task which the inventor feels is of vital importance. It deals with prediction of scrubber life, imminent failure, and outright warning. Without this form of monitoring the operator can become hypercapnic, which can lead to unconsciousness. We feel that there must be some mechanism which informs the operator how much time is remaining on the scrubber and/or if the breathing gas has a dangerous level of $CO_2$.

Determining the remaining scrubber life based on a single reading of $CO_2$ level in the breathing loop is difficult. Scrubber beds typically expire at an exponential rate and that decay rate onset is often non-linear. This exponential decay in scrubber performance is akin to the weak link in the chain. Once an area of the scrubber is used, it forms a channel. Channeling is also a term found in descriptions of scrubber beds. This channel allows the $CO_2$ to "Break-Through" without getting scrubbed. It is common in granular beds to find small finger like projections through the media when this channeling occurs.

The scrubber system will appear to be absorbing $CO_2$ normally with not much change in efficiency over time until “break-through” begins. Once “break-through” begins the entire scrubber failure progresses very quickly. Creating an algorithm which states that if the $CO_2$ level at the outlet is X, the Scrubber will expire at Y is a dangerous statistical game at best.

Measuring implies using a sensor. The most common type of $CO_2$ sensors are the Non Dispersive Infrared (NDIR) style. There are two major problems with these types of sensors. First: They are power hungry and will drain batteries quickly. Second: Water vapor plays havoc with the detection mechanism. High concentrations of water vapor and/or condensation absorb the infrared light (heat) in much the same way as $CO_2$. This causes these sensors to read falsely (producing a False Positive to be more exact).

In a rebreather, the breathing loop is at 100% relative humidity and it is a condensing environment. Water vapor is constantly being added from the operator’s lungs as well as from the scrubber media (from the scrubbing reaction). This means that it is a very tough environment for one of these types of sensors. The only chance for one of these sensors to function correctly (in a rebreather) is to find one that can be supported by a small battery and one where the gas can be dried prior to sensing.

The inventor believes that he has identified a NDIR sensor that will work in this application. It has a low power consumption rate and its wake-up time is less than 10 seconds. This short wake-up time means that it can be turned off to conserve power and then activated to take samples of the gas and then turned off again. We have spent a considerable amount of time developing a gas drying system for a $CO_2$ sensor. This drying mechanism relies on the pressure pulses within the breathing loop across the scrubber media. Based on our Computational Fluid Dynamics Studies (CFD), we believe we have a workable solution for a gas drier.

While it would be a perfect world if there were no pressure variations within the breathing loop these pressure variations are unavoidable in a rebreather system. With this system there are two different sources of pressure variation. The first comes from pure resistive loading across the scrubber media. The higher the gas velocity through the scrubber the greater the pressure drop across the scrubber. This resistive load corresponds to an increase in the operators’ exhalation pressure and decrease in inhalation pressure. These are directly related to the inhale/exhale volumetric flow-rate. Every effort must be made to reduce this resistance as it is directly perceived by the operator as additional Work of Breathing (WOB).

The second pressure variation is due to the tidal volume cycle on the elastic components of the counterlung. Both of these pressure variations are system inherent. The good news is that they can be put to work as a pumping mechanism for a gas drier for the $CO_2$ detection system.

Because scrubbers function as reactors in that there is a reaction zone which moves through the media as the media is consumed, it is possible to monitor where this reaction is occurring. In short, there is a reaction front which moves from the inlet to the outlet. Since this reaction is exothermic it is possible to determine where the reaction is at by monitoring the temperature along the length of the scrubber bed.

Most conductors respond to changes in temperature by changing electrical resistance. Higher temperatures result in higher resistance. The inventor fabricated a sensor consisting of a fine copper wire, such as, for example 22 gauge wire, that is wound into a coil on a plastic mandrel. This coil is tapped at regular intervals so that the resistance, and thus the temperature, could be monitored.

The inventor did see a resistance change over temperature but the scale and range of change are quite small. At room temperature there is a reading over the entire coil of about 6.9Ω. By warming it up with a hot air gun the resistance increased to 8.0Ω. The theory worked but the ohmic range was too narrow to be practical with copper wire. A nichrome or Ni—Fe blend of wire which has a higher ratio of resistance change to temperature might have worked but would be too costly for a production solution. The inventor also had concerns regarding the coil acting as a radio receiver. The coil based temperature sensor idea has been abandoned.

Thermocouples and/or thermistors provide the best solution to measure the temperature patterns in the scrubber. Alternately, it may be best to work around this by simply sampling gas at various points within the scrubber media and directly routing those by the $CO_2$ sensor. Since the areas in front of the reaction zone have been used up, the $CO_2$ levels in these areas should be high (around 5% SEV). $CO_2$ levels behind the reaction zone (unused) should yield much lower $CO_2$ levels (around 0.5% SEV). By sampling the $CO_2$ levels along the scrubber bed it should be possible to determine where the reaction front is located, similar to the results from the temperature probes. It will also be possible to determine if the $CO_2$ levels are too high or if “Break-Through” is eminent. During times of high work load it may be possible to over-breathe the scrubber. This means that large quantities of $CO_2$ could get by the media and back to the operator and that the thermal monitoring stick would not be able to correctly catch this, only the $CO_2$ sensor/detector could. Scrubber media usage is often non-linearity at different flow rates. The design of the new scrubber system and media, which is illustrated in FIGS. 16A through 16F, allows for gas sampling from within the media at the midpoint (Note the Gas Transfer Screen) and at the exit. This gas sampling is pumped up to the gas drying system and into the $CO_2$ sensor using tidal breathing pressure created from the counterlung system. Rather than taking the pressure drop across the scrubber media, the inventor has chosen a more positive displacement method. This pumping mechanism is located inside the rebreather head and is part of the gas drying system.

The operators exhaled breath is approximately 5% $CO_2$ SEV (standard equivalent volume). As the scrubber media begins to get used, small amounts of $CO_2$ will make it to this midpoint sampling port. As it gets combined with the gas from the outlet it gets diluted by half. If the output of the gas sampling results in a $CO_2$ level of 2.5% SEV and it is relatively constant it can be directly inferred that the reaction is at the midpoint of the scrubber system. If it is at 4% SEV the scrubber is either being dramatically overworked and is bypassing $CO_2$, or there is only about ½ inch of remaining scrubber media. In either case it would be a really good time to get off the loop.

The inventor was concerned with is the scrubber status and its remaining life. By characterizing the $CO_2$ output in both standard breathing modes and when it is being over-breathed it should be possible to develop a very reliable warning system to either alert the operator that he is over-breathing the system or needs to get off of the breathing loop because the scrubber is used up and the loop is going hypercapnic The inventor believes that he has arrived at an acceptable solution for scrubber remaining life monitoring, gas drying and $CO_2$ level measurement. The Extruded Aluminum Tube System (Note FIG. 17) which connects the Scrubber System to the Rebreather Head serves several purposes. The first and primary function aside from connecting the two systems is to serve as a heat exchanger and hence the cooling fins on the outside. The second function is to act as a water vapor condenser for the $CO_2$ monitoring gas sample. The previous design of the drying system had multiple condenser disks located before the hydrophobic membrane. These disks have been removed to make room for the pumping system as detailed in following paragraphs.

Figure 1A:
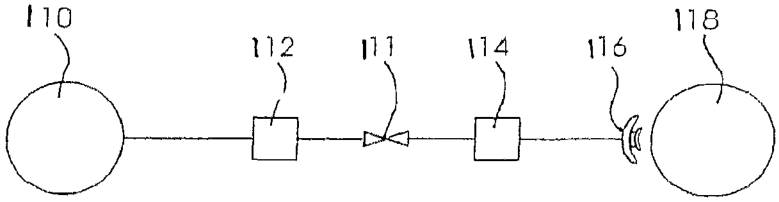
FIG. 1A (PRIOR ART)
FIG. 1A is a semi-schematic generalized block level diagram of an open circuit breathing apparatus in accordance with the prior art
Figure 1B:
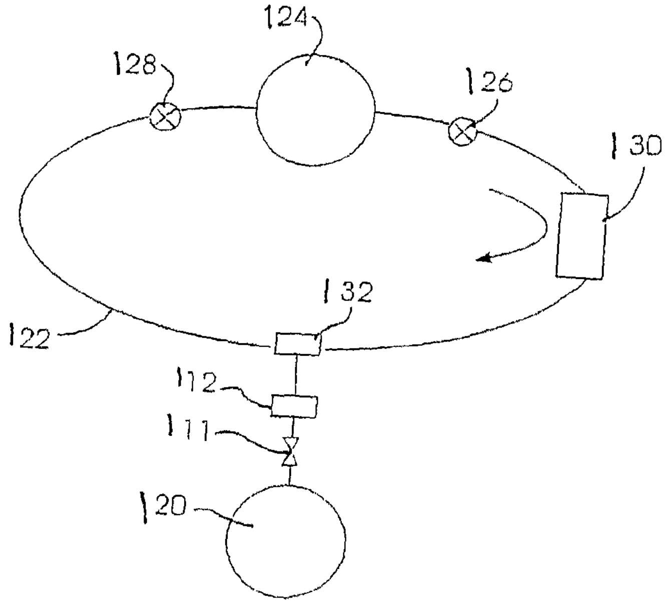
FIG. 1B (PRIOR ART)
FIG. 1B is a semi-schematic generalized block level diagram of a semi-closed circuit rebreather system, in accordance with the prior art
Figure 1C:
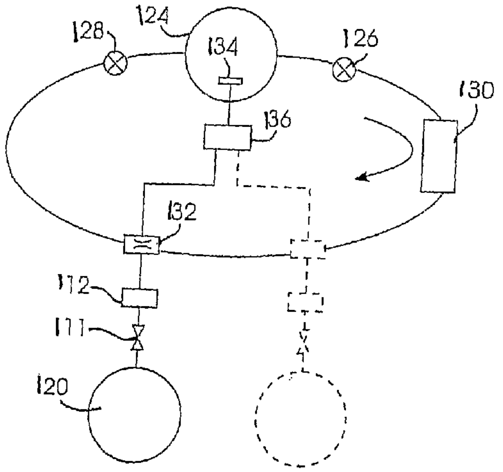
FIG. 1C (PRIOR ART)
FIG. 1C is a semi-schematic generalized block level diagram of a closed circuit rebreather system including an oxygen rich breathing gas supply tank, diluent gas supply tank, and an oxygen sensor, in accordance with the prior art.
Figure 17:
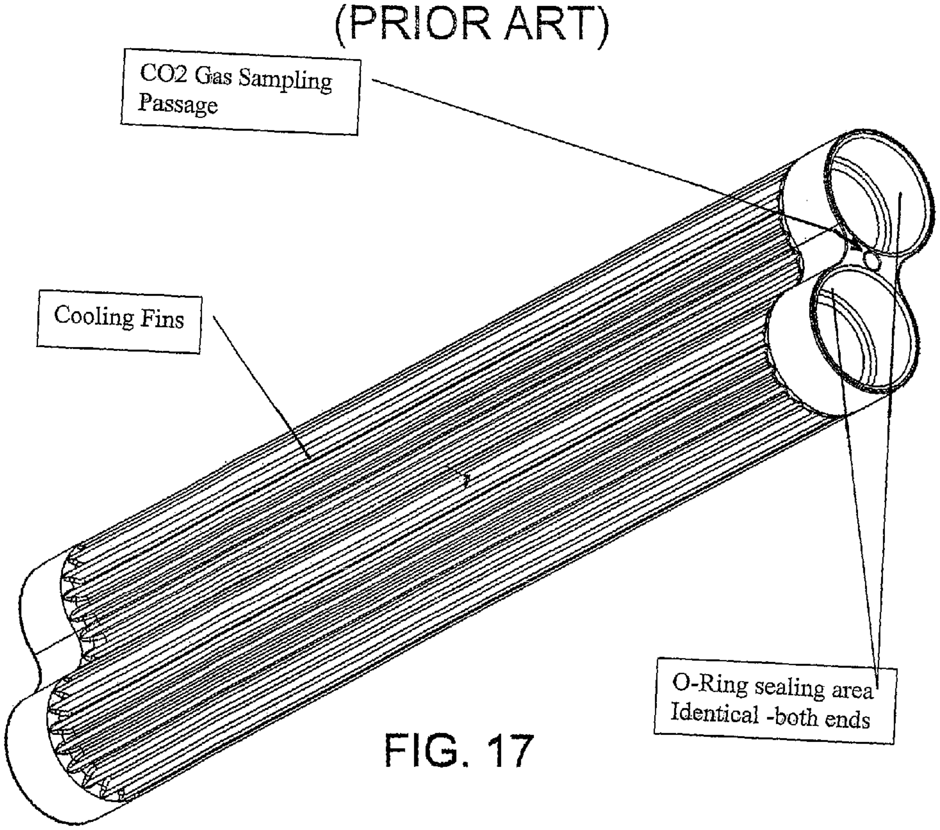
FIG. 17 illustrates a tubing system for connecting the scrubber system shown in FIG. 16 to the head assembly shown in FIG. 3.

An Extruded Aluminum Tubing System 16 that is self captured on the ports from the Flow Router and the Scrubber System is illustrated in FIG. 17. It is designed to mechanically float between these two systems which means that small alignment errors between the rebreather head assembly 20 and scrubber system 22 can be tolerated and will not create stress on individual components.

A gas drying system, as illustrated in FIGS. 18A through 18G, includes a diaphragm based pumping mechanism in the lower portion of the unit. Simple rubber flapper valves are used to control directionality. Condensation disks have been removed to allow for the packaging of this pumping system.

FIGS. 19A through 19G detail the flow ports of the pumping system. This piece is designed to hold the rubber disks which act as the valves. The pumping system is located in the housing of the gas dryer on tapers. These tapers will most likely be coated with silicone to enhance sealing. The dryer system is primarily a cyclonic separator. The goal was to slightly reduce the humidity and prevent condensation on the sensor. The cyclonic essentially spins the excess vapor out of the gas and also heats the gas slightly to raise the dew point. The inventor has performed CFD analysis on this part and testing this theory with encouraging results. CFD was an integral design tool in the redesign of the scrubber system. It took almost ten significant design iterations to get the flow totally smooth over the entire scrubber media. The present scrubber canister design provides significant gas dwell time at the end cap area where the cooling fins are located The gas is repeatedly forced against the end cap to aid in heat transfer.

The scrubber system is located about as far away from this gas drying system as is possible, while this is perfect from a gas cooling and condensing standpoint it also means that a larger volume of gas must be pumped to get a sample. It may require ten or more breathing cycles before the condition inside the scrubber is measured. A potential area of concern is pathogen growth in the gas sampling passageways. As there will be condensation within these passages it will be possible for things to grow. However, the inventor contemplates drying the passages by blowing in dry air into the sampling port after every use. This could simply be part of the maintenance protocol. Another solution would be to coat the inner surfaces with an antimicrobial compound which would kill anything before it grows. The inventor has developed a hybrid system which uses the pressure pulsations from the tidal rhythm of the boost pressure in the counterlung system to pump the gas samples from 2 points within the scrubber system. This gas detection system will alert the operator that the scrubber is used up, prior to total scrubber failure.

Regarding Objective 4, Packaging of Solution and User Interface, the package size for this replacement system needs to be as small and light as possible while providing substantially longer operational times. The design is intuitive so that a crew member should be able to operate the rebreather system 10 with minimal training. There are shown in FIGS. 20A through 20L, sectional views of the rebreather system 10 detailing the control barrel placed in different positions. In FIGS. 20A through 20L, Section A-A is sliced through the outlet of the system, while Section B-B slices through the inlet of the system. Thus, in the section A-A views, the port that points upward is the outlet of the unit and returns the gas for operator inhalation while in the section B-B views, the port that points upward is the inlet and routes the operator's exhalation breath into the overpressure valve and/or rebreather system.

FIGS. 20A through 20D depict the control barrel lever in the downward position. In this position oxygen is off. System monitoring is off. Open circuit and closed circuit rebreather functionality is disabled. The rebreather Counterlung and Scrubber System as well as the Demand Valve System are sealed from the surrounding atmosphere.

FIGS. 20E through 20H depict the control barrel lever in the horizontal position. In this position oxygen is on. System monitoring is off. Open circuit functionality is enabled and closed circuit rebreather functionality is disabled. The rebreather Counterlung is sealed from the surrounding atmosphere.

FIGS. 20I through 20L depict the control barrel lever in the upward position. In this position oxygen is on. System monitoring is on. Open circuit functionality as well as closed circuit Rebreather functionality is enabled. The rebreather Counterlung is functional and opened to the breathing loop.

At its most condensed, an oxygen system designed for aircrews must maintain life support from sea level to 50000 ft. At elevations above 43000 ft it is mandatory to boost the pressure at the alveolar tissues so that the inspired oxygen is maintained at a non-hypoxic level.

The transition from prior art mixed gas closed circuit rebreathers to an oxygen rebreather that is utilized in the present invention means that there is now only oxygen and no dilution (provided a proper purge has been made and only pure oxygen is used). Therefore, the $PPO_2$ will be 1.0 ata at sea-level and steadily decrease as altitude increases (until boost pressure system is active). Pressure boost will effectively start at elevations above 33700 ft and automatically ramp up to the required level at 43000 ft and above. There will be a nominal boost of approximately 0.5 inch $H_2O$ at all times for the rebreather use. This insures that leaks vent oxygen out of the breathing loop rather than venting gas (nitrogen, $CO_2$, CO, hydrocarbons, etc.) into the loop.

The present invention meets the following system requirements:

Fail safely regardless of operational mode.

Act as full replacement of the current life support system and function over the same flight envelope or expand that envelope over the current systems.

Integrate the components into a small, lightweight unit which conforms to all applicable air-worthiness and safety requirements for military aircraft.

Be compatible with onboard oxygen systems.

Dramatically extend the useable oxygen supply over the current systems.

Be similar in size and shape to the current system such as the Carlton Life Support System Model OS1006 which uses an A-21 style regulator and MIL-C-5886E style gas cylinder.

Provide pressure breathing as required at altitude.

Automatically adjust the pressure breathing boost pressure as altitude changes.

Allow the rebreather system to be bypassed and function strictly as an open circuit gas supply system.

Maintain boost pressure while switching between rebreather and open circuit modes.

Prevent over-boost of the operators' lungs with a pressure balance relief system and ultimate relief system.

Not cause heat fatigue of the operator due to the reaction temperatures created inside the scrubber system.

Have an easily replaceable $CO_2$ scrubber media. Ideally a solid state insert cartridge.

Reliably predict $CO_2$ scrubber use and estimate the remaining duration via gas sampling to a $CO_2$ sensor (at various points within the system (Scrubber)).

Reliably warn the operator if the $CO_2$ scrubber is no longer functional via light and/or sound.

Automatically deflate the counterlung system when not in use (Open Circuit or System Off modes).

Consistently deflate the counterlung into the storage configuration.

Have a monitoring system which is self calibrating: Oxygen (if used), $CO_2$ and Pressure sensors.

Be self-purging of residual nitrogen or a monitoring system must alert the operator that active purging is required.

Allow the user to manually over-ride the system and add oxygen when needed in both rebreather and open circuit modes.

Allow automatic and manual venting of rebreather system via a purge-valve and pressure-relief valve(s) (balanced and ultimate relief).

Use quick disconnections, such as CRU series if feasible with a dual hose configuration for rebreather system.

Be compatible or adaptable to current flight masks (such as Gentex MBU series) and other personal oxygen delivery devices used by aircrews in open circuit mode.

Reliably monitor the cylinder pressure.

Be easily maintained and cleaned after use.

Not allow disease transmission from pathogen growth in any part of the system.

The rebreather system 10 also includes a status display screen that uses low power liquid crystal display(s) (LCD) readout in addition to light emitting diodes (LED's or OLED's) and a sound creation system (piezo speaker/buzzer). Additionally, the system 10 may optionally include Use a CO sensor to monitor carbon monoxide and possible hydrocarbon introduction into the breathing loop. The system also uses existing oxygen bottles as a cost savings measure and may include an override to produce "Emergency Boost" of at least 13 inches $H_2O$.

The results of CAD work show that the system 10 has been packaged in nearly the same size as the original walk around system, there are still issues with weight and overall system bulk. The counterlung system when inflated requires about 9 liters of volume to function properly (mostly unavoidable). Because the outer counterlung is elastic, it will collapse to a storage state that closely drapes the oxygen cylinder. While further refinement is definitely possible (with any design) we have created a design which embodies all of the requirements and is the same size as the current system (and approaches the original weight), all while offering about 2 hours of effective gas supply.

Regarding Objective 5, modification of the $PPO_2$ controller for altitude use, the inventor has developed the design of a closed circuit rebreather system with an automatic dilution system strictly for altitude use. This system was originally designed to meet initial requirements of constant $PPO_2$ of 0.21 ata. The inventor had planned to use the controller designed for an underwater rebreather system. This objective was originally to determine the best way to control the life support gas given the sensor set. The inventor developed the full controls system to regulate the $PPO_2$ in the breathing loop of a closed circuit rebreather system with most of the controls work completed for the underwater rebreather system. In developing the controls strategy the inventor also created the plant. The plant was one of the more difficult items to model as it included the diver/operator (gas consumption/mixing), counter lung system (gas addition/mixing and gas venting), and the rebreather head (gas measurement/mixing). All of the controls modeling was done using Matlab SimuLink. Having everything modeled allowed for determinations of gas usage and thus efficiency of a mixed gas rebreather vs. a pure oxygen rebreather. It also allowed us to model various counter lung systems to determine which one would yield the lowest pressure variations over the tidal breathing cycle. However, the design of the mixed gas rebreather was abandoned because of the change in direction towards a closed circuit oxygen rebreather. With regard to gas usage, the work done in this area was verified by the personal experience of the inventor who dives underwater rebreathers. It also helped the inventor to determine the best counterlung system for pressure breathing. Simulation helped the inventor to appropriately size and determine the level of elasticity needed for proper pressure boost functionality. After spending all of the time developing a controller for the underwater rebreather system it can truly be said that the beauty of an Oxygen Rebreather is that it requires no electronics to provide full life support. If the batteries are dead or a sensor is malfunctioning, it does not matter. The sensors and monitoring electronics on the proposed system are strictly for monitoring. There is dramatically reduced danger of an operator going hypoxic on an oxygen rebreather. This statement cannot be made for a mixed gas system. Most of the oxygen sensors used in these applications function based on a galvanic principle. These sensors essentially rust themselves to death and output a voltage based on the corrosion rate. The rate of this corrosion is directly equivalent to the oxygen partial pressures the sensors are exposed to. Storing these sensors in pure oxygen will shorten their lives from approximately 2 years in air to less than a couple of months. Storing these sensors in an anoxic atmosphere means that they will not immediately work as they require a wake up time before use.

With underwater rebreathers, it is normal to make a predive check to insure that the oxygen sensor(s) have been properly calibrated. This altitude rebreather may be stored for long periods between uses. This means that the oxygen sensor will probably not be calibrated when needed. Requiring the operator to do this at altitude is possible but error prone and time consuming. Requiring the operator to calibrate the unit before flight is an option but not an attractive one, as the system may not be needed and this calibration routine will take time.

If the one is thinking that there is risk here, it should be considered that the above issues are simply for the monitoring system. Sensor calibration for actual $PPO_2$ control, as required in closed circuit mixed gas rebreather, is absolutely required prior to use. These complications are another major reason why an oxygen rebreather is an advantage over a mixed gas rebreather for this application. Galvanic oxygen sensors have their place, but it is probably not in this application simply due to the complications of proper calibration, even if it is only for monitoring The inventor has found another technology which offers promise. Ocean Optics, Inc. has oxygen sensors which function on a totally different principle. These sensors rely on dynamic fluorescence quenching. This company has created a coating that gives off fluorescence when exposed to oxygen and a light source (blue light). This blue light is first shined onto the treated surface and then turned off. The decay rate of the florescence is directly related to the oxygen partial pressure. The beauty of this system is that the sensor element which is coated with the fluorescing material can be almost anything, such as, for example, glass, plastic or metal. The sensor/detector is a fiber-optic lead. The same lead is used to shine the blue light to cause the excitation and to read the resulting fluorescence. This technology provides that the sensing element will live indefinitely while saturated with oxygen provided there is no light source shining on it. The only thing that decays the sensor is the light. What this means is the system could be stored for years without use and would be ready to go when needed. Another plus to this technology is that it is unaffected by high humidity or condensation. This same sensor can measure oxygen levels in gas as well as in liquid. The inventor believes that it may be possible to use this same technology for detecting carbon dioxide although they do not have a product currently. If this same technology can be applied to the measurement of both gasses it will simplify the overall design of the rebreather system.

Currently, electronics are planned for the Air Crew Altitude Rebreather System that include three primary sensors, namely:

(1) Oxygen sensor (galvanic or optical): The role of this sensor is to monitor the oxygen level within the breathing loop to insure that a proper purge has been made. The other reason is to alert the operator if inert gas is building up. If less that 100% oxygen is used, inert gas will build up in the loop and will need to be vented.

(2) $CO_2$ sensor: This sensor will alert the operator if the scrubber is malfunctioning and the operator needs to get off of the breathing loop by switching from rebreather to open circuit mode. It will function in a similar manner as a Temperature Probe Stick and it will identify the reaction area inside the scrubber system. Essentially, it will fulfill two purposes, identify remaining scrubber time and warn the operator of elevated $CO_2$ levels within the breathing loop.

(3) Absolute Pressure sensor: This sensor is needed to condition the partial pressure outputs of the oxygen and $CO_2$ sensors to fractional levels for use in the monitoring electronics and software.

The present invention also contemplates making the rebreather semi-closed circuit. Think of it as a fully closed circuit rebreather with a leak. Upon first look it does not make immediate intuitive sense to vent an oxygen rebreather however there are a few advantages (optimal gas conservation not being one of them). A semi-closed circuit rebreather would automatically replace the gas in the breathing loop by venting the old and requiring the new to be added (via the demand valve regulator).

If the operator does not make a full purge of the system initially this leak would slowly cause the breathing gas to normalize towards the supply gas concentration, which should be nearly 100% oxygen. Another advantage is slightly less obvious. If the breathing loop is fully closed and the supply gas is less than 100% oxygen, the breathing loop will slowly fill with inert gas as the operator consumes the oxygen out of the loop.

In a fully closed circuit rebreather system this will result in the slow drop in $PPO_2$. This potential drop in $PPO_2$ is another reason to have a monitoring system. With this monitor, the operator is alerted that the loop needs to be purged. This requires the operator to take action. With a semi-closed breathing loop, oxygen level monitoring is not needed because the build up of inert gas is automatically vented (without user intervention). This means that an oxygen sensor would not be needed.

From a design standpoint it now makes little or no difference to system packaging whether the closed system is used or not or if the system is converted to semi-closed operation. The inventor has essentially ruled out galvanic oxygen sensors due to the calibration requirements and short service life. A galvanic oxygen sensor cell adds significantly more weight than the optical system.

As far as the system design goes the oxygen sensor is now placed very close to the outlet of the rebreather. It is located in front of the mushroom valve covering the boost chamber. This means that it will have the best chance to measure the actual inspired gas to the operator. Placing the oxygen sensor in front of the mushroom valve in front of the boost chamber helps to insure sensor reliability. As oxygen is added to the breathing loop it must pass over the sensor. This added oxygen is very dry and will help to keep the sensor element free of condensation (which could alter the reading).

With regards to this added oxygen affecting the reading of the sensor, keep in mind that oxygen is typically only added when the counterlung is empty and hence gas is not moving through the scrubber. The operator will be getting the pure oxygen that the sensor will read. Digital filtering within the monitoring system is another simple way of minimizing these concerns of spikes in the oxygen concentration level. Keep in mind that the oxygen sensor is there for monitoring purposes only, not $PPO_2$ control.

The inventor believes that the rebreather system 10 for emergency and walk around use is not only feasible but that it will have many benefits over existing rebreather systems. Pressure breathing via the counterlung inside an elastic bladder is effective and practical. The counterlung system can be made to collapse snuggly around the oxygen tank when not in use so storage is also simplified.

The inventor further believes that it is possible to create a rebreather system which will be intuitive for the end user to operate. This system will have the common use of pressure breathing found in the current walk around system and will have both open circuit and closed circuit modes. The pressure breathing mechanism will not require user adjustment as it will be fully automatic.

The present invention packages in a space nearly the same as the current walk around system. The inventor believes that this size of this system can be dramatically reduced with a different higher pressure cylinder and that the weight could be further reduced to approximately 9 lbs.

The present invention provides the following benefits:

(1) Simplification of Safe Use: A system for aircrews must function in a familiar manner to what is used now. The technology of the rebreather system 10 is advanced to a point where training is minimal and the end use is simple and above all safe.

(2) Simplification of Maintenance: Prior art rebreather systems require significant user attention before, during and after use. For a rebreather system to be practical for aircrews it must minimally impact their workloads. While rebreathers will always require more work than their open circuit counterparts the design of the present invention should minimize this burden.

(3) Reliable Detection of $CO_2$ and/or Scrubber Status:

(a) Standard infrared $CO_2$ detectors have not proven reliable in rebreathers due to the high humidity and condensation affecting the transmission of light/heat to the sensor optics. This is a gas conditioning gas drying problem which the inventor believes he has overcome with the present invention.

(b) The thermal wave-front inside the scrubber system is also a good indicator of where the primary reaction is at. The inventor believes that he has a novel work-around patented temperature mapping which uses a $CO_2$ sensor to sample multiple points inside the scrubber. The inventor believes that his new design will also map the reaction area and predict remaining scrubber life and will be much more robust and failsafe. Development is needed to verify this.

(4) Dynamic Venting and Control of Breathing Loop Volume: As altitude increases the ambient pressure drops and the gas in the breathing loop expands. The overall gas volume will need to be lowered by venting to the surrounding atmosphere. This is done in a manner which will not damage the operators' lungs.

In prior art systems, Galvanic oxygen sensor cells utilized in oxygen sensors have many problems which make them unacceptable for this application. The present invention contemplates either removing the Sensor and using a Semi-Closed Rebreather approach or adopting a new technology from Ocean Optics, Inc.

In prior art systems, if the mushroom valve fails, boost pressure can build-up. Also, in prior art systems, should the regulator free-flow or fail open, there is a need to vent that gas directly. The present invention contemplates installing a High Flow Mushroom Valve on the Control Barrel on the Outlet Side End and installing a flow restrictor to slow the pressure balance rate between the boost chamber and the inlet pressure relief mechanism diaphragm/bladder.

In prior art systems, the outer counterlung inflates during open circuit use, but will not deflate when system is shut down. The present system contemplates transferring boost pressure to the counterlung only when in rebreather mode by a Boost Routing Sleeve mounted on the Control Barrel. When Control Barrel is in the "off" or "open circuit" position, the boost pressure in the counterlung is bled off by passageways on the Boost Routing Sleeve. When the Control Barrel is in the off position the purge button will vent the inner counterlung, while the Boost Routing Sleeve vents the outer gas volume.

In prior art systems, the heat generated by the $CO_2$ scrubber system may not be properly managed. The present invention contemplates utilizing a heat sink and adding cooling fins on the inside and outside of the scrubber canister caps and center hoop to radiate and convect away excess heat. Also, the scrubber system is remotely mounted from the Rebreather Head and pneumatically connect them through a heat exchanger.

In prior art systems, the electronics need to be correctly packaged such that there are no loose cables which can get snagged or sheared off. The electronics system needs to be sealed and protected from the breathing loop and surrounding atmosphere. The batteries need to be in a sealed enclosure separate from the breathing loop. The present invention contemplates that the electronics and battery systems are now packaged in a sealed enclosure integral to the rebreather head but separate from the breathing loop. The temperature stick concept has been abandoned in favor of a direct gas sampling system. This gas sampling system will determine both the remaining scrubber life and dangerous $CO_2$ levels. Development work continues on a gas sampling solution. The concept is elegant and simple and the inventor is confident that this is a real solution to a problem that has plagued these machines since their inception.

A flow chart illustrating the interconnection of the components described above and the operation of the rebreather system 10 is provided in FIG. 21.

In conclusion, the development of the rebreather system 10 has been an exercise in optimal packaging. What has been designed is a state of the art life support system which is capable of multiple roles; military, civic and commercial. A considerable amount of design time has gone into the present invention.

The inventor is confident in the high level of engineering that has gone into this system and the modularity of the new design. The new design which places the Scrubber and Tank In-line offers better overall weight balance, better cooling and dramatically improved streamlining. The inventor believes that the modularity of this unit will be one of its greatest strengths.

While the invention has been described and illustrated in terms of an aircrew rebreather system, the inventor also contemplates utilizing the system in other environments, such as, for example, by firemen entering building filled with smoke and other hazardous fumes or by mine rescue personnel by simply mounting the system upon a backplate (not shown). The resulting system would be lighter that prior art Scott-Packs. Additionally, as alluded to above, the system may utilized underwater by divers, in which case the control unit adjusts the pressure of the gas supplied to the diver as a function of the depth of water.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A rebreather system comprising:

a rebreather head assembly having a breathing hose connector mounted thereupon;

a double conterlung that includes an inner air bladder disposed within an outer air bladder with a void defined between said inner and outer bladders connected to said rebreather head assembly, said counterlung outer bladder being elastic and flexible and said counterlung inner bladder being non-elastic but flexible;

a supply of oxygen gas connected to said rebreather head assembly;

a scrubber canister connected to said rebreather head assembly, said rebreather head assembly operative to selectively add oxygen gas to said conterlung to maintain the oxygen level within the system as function of the surrounding environment; and a single control device disposed within said rebreather head assembly and operative to selectively switch between one of an oxygen off mode of operation, an oxygen on/open circuit mode of operation and an oxygen on/closed circuit mode of operation, said control device also being selectively operative to pressurize said void between said inner and outer to provide a pressure boost to said inner counterlung bladder.

2. The rebreather system according to claim 1 further including a gas drying system.

3. The rebreather system according to claim 2 further including a breathing mask connected to said rebreather head assembly by a pair of hoses.

4. The rebreather system according to claim 2 wherein said gas drying system includes internal channels that are operative to swirl the gas into a vortex such that moisture is expelled from the gas.

5. The rebreather system according to claim 4 wherein the system is adapted for use by aircrew and further wherein said rebreather head assembly is operative to selectively actuate valves within said rebreather head assembly to maintain the oxygen level within the system as function of altitude.

6. The rebreather system according to claim 4 wherein the system is adapted for use by a diver and further wherein said rebreather head assembly is operative to selectively actuate valves within said rebreather head assembly to maintain the oxygen level within the system as function of water depth.

7. The rebreather system according to claim 1 wherein said counterlung is disposed within a rigid enclosure.

* * * * *